United States Patent
Freese et al.

(10) Patent No.: US 9,441,149 B2
(45) Date of Patent: Sep. 13, 2016

(54) METHODS FOR MONITORING THE FORMATION AND TRANSPORT OF A TREATMENT FLUID USING OPTICOANALYTICAL DEVICES

(75) Inventors: Robert P. Freese, Pittsboro, NC (US); Christopher M. Jones, Houston, TX (US); Michael T. Pelletier, Houston, TX (US); Rory D. Daussin, Spring, TX (US); David M. Loveless, Duncan, OK (US); Johanna Haggstrom, Duncan, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 974 days.

(21) Appl. No.: 13/198,915

(22) Filed: Aug. 5, 2011

(65) Prior Publication Data

US 2013/0032334 A1 Feb. 7, 2013

(51) Int. Cl.
| | |
|---|---|
| C09K 8/62 | (2006.01) |
| G01N 21/31 | (2006.01) |
| G01N 21/85 | (2006.01) |
| E21B 43/26 | (2006.01) |
| E21B 43/28 | (2006.01) |
| E21B 49/08 | (2006.01) |

(52) U.S. Cl.
CPC ............... *C09K 8/62* (2013.01); *E21B 43/26* (2013.01); *E21B 43/28* (2013.01); *G01N 21/31* (2013.01); *G01N 21/85* (2013.01); *E21B 2049/085* (2013.01)

(58) Field of Classification Search
CPC ... E21B 47/065; E21B 47/124; E21B 49/008
USPC .................................................... 166/250.01
See application file for complete search history.

(56) References Cited

U.S. PATENT DOCUMENTS

| | | | |
|---|---|---|---|
| 4,761,073 | A | 8/1988 | Meltz et al. |
| 4,806,012 | A | 2/1989 | Meltz et al. |

(Continued)

FOREIGN PATENT DOCUMENTS

| | | |
|---|---|---|
| EP | 2320027 A1 | 5/2011 |
| FR | 2954563 A1 | 6/2011 |

(Continued)

OTHER PUBLICATIONS

International Search Report and Written Opinion for PCT/US2012/046898 dated Apr. 5, 2013.

(Continued)

*Primary Examiner* — Catherine Loikith
*Assistant Examiner* — Ashish Varma
(74) *Attorney, Agent, or Firm* — McDermott Will & Emery LLP; Craig Roddy

(57) ABSTRACT

In or near real-time monitoring of fluids can take place using an opticoanalytical device that is configured for monitoring the fluid. Fluids can be monitored prior to or during their introduction into a subterranean formation using the opticoanalytical devices. Produced fluids from a subterranean formation can be monitored in a like manner. The methods can comprise providing at least one source material; combining the at least one source material with a base fluid to form a treatment fluid; and monitoring a characteristic of the treatment fluid using a first opticoanalytical device that is in optical communication with a flow pathway for transporting the treatment fluid.

22 Claims, 3 Drawing Sheets

(56) References Cited

U.S. PATENT DOCUMENTS

| | | |
|---|---|---|
| 5,186,255 A | 2/1993 | Corey |
| 5,399,854 A | 3/1995 | Dunphy et al. |
| 5,431,227 A | 7/1995 | Montgomery et al. |
| 5,493,390 A | 2/1996 | Varasi et al. |
| 5,540,825 A | 7/1996 | Yeung et al. |
| 5,680,900 A | 10/1997 | Nguyen et al. |
| 5,737,076 A | 4/1998 | Glaus et al. |
| 5,996,690 A | 12/1999 | Shaw et al. |
| 6,016,191 A | 1/2000 | Ramos et al. |
| 6,091,504 A | 7/2000 | Walker et al. |
| 6,198,531 B1 | 3/2001 | Myrick et al. |
| 6,268,911 B1 | 7/2001 | Tubel et al. |
| 6,529,276 B1 | 3/2003 | Myrick |
| 6,576,188 B1 | 6/2003 | Rose et al. |
| 6,729,400 B2 | 5/2004 | Mullins et al. |
| 6,755,978 B2 | 6/2004 | Oddie |
| 6,880,566 B2 | 4/2005 | Newman |
| 7,123,844 B2 | 10/2006 | Myrick |
| 7,236,237 B2 | 6/2007 | Schmilovitch et al. |
| 7,332,094 B2 | 2/2008 | Abney et al. |
| 7,472,748 B2 | 1/2009 | Gdanski et al. |
| 7,623,233 B2 | 11/2009 | Freese et al. |
| 7,671,973 B2 | 3/2010 | Van Beek et al. |
| 7,697,141 B2 | 4/2010 | Jones et al. |
| 7,712,527 B2 | 5/2010 | Roddy |
| 7,789,171 B2 | 9/2010 | Grayson et al. |
| 7,834,312 B2 | 11/2010 | Lievois et al. |
| 7,834,999 B2 | 11/2010 | Myrick et al. |
| 7,875,455 B1 | 1/2011 | Li et al. |
| 7,911,605 B2 | 3/2011 | Myrick et al. |
| 7,920,258 B2 | 4/2011 | Myrick et al. |
| 7,934,556 B2 | 5/2011 | Clark et al. |
| 8,253,619 B2 | 8/2012 | Holbrook et al. |
| 8,345,234 B2 | 1/2013 | Myrick et al. |
| 8,547,556 B2 | 10/2013 | Irani |
| 8,619,256 B1 | 12/2013 | Pelletier et al. |
| 8,780,352 B2 | 7/2014 | Freese et al. |
| 8,823,939 B2 | 9/2014 | Freese et al. |
| 8,879,053 B2 | 11/2014 | Freese et al. |
| 8,908,165 B2 | 12/2014 | Tunheim et al. |
| 8,912,477 B2 | 12/2014 | Freese et al. |
| 8,941,046 B2 | 1/2015 | Freese et al. |
| 8,960,294 B2 | 2/2015 | Freese et al. |
| 8,997,860 B2 | 4/2015 | Freese et al. |
| 9,013,698 B2 | 4/2015 | Freese et al. |
| 9,013,702 B2 | 4/2015 | Freese et al. |
| 9,019,501 B2 | 4/2015 | Freese et al. |
| 9,074,990 B2 | 7/2015 | Freese et al. |
| 9,080,943 B2 | 7/2015 | Freese et al. |
| 9,103,716 B2 | 8/2015 | Tunheim et al. |
| 9,103,720 B2 | 8/2015 | Russell et al. |
| 9,103,767 B2 | 8/2015 | Freese et al. |
| 9,142,002 B2 | 9/2015 | Dutton |
| 9,170,154 B2 | 10/2015 | Myrick et al. |
| 9,170,208 B2 | 10/2015 | Tunheim et al. |
| 9,176,052 B2 | 11/2015 | Tunheim et al. |
| 9,182,282 B2 | 11/2015 | Myrick et al. |
| 9,182,355 B2 | 11/2015 | Tunheim et al. |
| 9,206,386 B2 | 12/2015 | Tunheim et al. |
| 9,222,348 B2 | 12/2015 | Freese et al. |
| 9,222,892 B2 | 12/2015 | Tunheim et al. |
| 9,261,461 B2 | 2/2016 | Tunheim et al. |
| 2001/0020675 A1 | 9/2001 | Tubel et al. |
| 2001/0023614 A1 | 9/2001 | Tubel et al. |
| 2002/0023752 A1 | 2/2002 | Qu et al. |
| 2002/0109080 A1 | 8/2002 | Tubel et al. |
| 2002/0154315 A1 | 10/2002 | Myrick |
| 2003/0056581 A1 | 3/2003 | Turner et al. |
| 2003/0143580 A1 | 7/2003 | Straus |
| 2003/0145988 A1 | 8/2003 | Mullins et al. |
| 2004/0045705 A1 | 3/2004 | Gardner et al. |
| 2004/0129884 A1 | 7/2004 | Boyle et al. |
| 2004/0179194 A1 | 9/2004 | Schmilovitch et al. |
| 2006/0102343 A1 | 5/2006 | Skinner et al. |
| 2006/0142955 A1* | 6/2006 | Jones .................... E21B 47/102 702/32 |
| 2006/0158734 A1 | 7/2006 | Schuurmans et al. |
| 2006/0183183 A1 | 8/2006 | Felkner et al. |
| 2007/0095528 A1* | 5/2007 | Ziauddin et al. .......... 166/252.3 |
| 2007/0114372 A1 | 5/2007 | Lievois et al. |
| 2007/0177240 A1 | 8/2007 | Van Beek et al. |
| 2007/0215385 A1 | 9/2007 | Anderson |
| 2007/0248488 A1 | 10/2007 | Denkewicz |
| 2007/0281870 A1 | 12/2007 | Robb et al. |
| 2007/0282647 A1 | 12/2007 | Freese et al. |
| 2007/0291251 A1 | 12/2007 | Rensen et al. |
| 2008/0000635 A1 | 1/2008 | Rioufol et al. |
| 2008/0041594 A1 | 2/2008 | Boles et al. |
| 2008/0094623 A1 | 4/2008 | Schuurmans et al. |
| 2008/0133193 A1 | 6/2008 | Gdanski et al. |
| 2008/0166720 A1 | 7/2008 | Hsieh et al. |
| 2008/0217011 A1 | 9/2008 | Pauls et al. |
| 2008/0262737 A1 | 10/2008 | Thigpen et al. |
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick et al. |
| 2009/0073433 A1 | 3/2009 | Myrick et al. |
| 2009/0087912 A1 | 4/2009 | Ramos et al. |
| 2009/0097024 A1 | 4/2009 | Blackburn et al. |
| 2009/0154288 A1 | 6/2009 | Heathman |
| 2009/0182693 A1 | 7/2009 | Fulton et al. |
| 2009/0205821 A1 | 8/2009 | Smith |
| 2009/0216504 A1 | 8/2009 | Priore et al. |
| 2009/0219538 A1 | 9/2009 | Myrick et al. |
| 2009/0219539 A1 | 9/2009 | Myrick et al. |
| 2009/0219597 A1 | 9/2009 | Myrick et al. |
| 2009/0245718 A1* | 10/2009 | Li .......................... B82Y 20/00 385/12 |
| 2009/0305330 A1 | 12/2009 | Kroon et al. |
| 2010/0006292 A1 | 1/2010 | Boles et al. |
| 2010/0042348 A1 | 2/2010 | Bakker |
| 2010/0050905 A1 | 3/2010 | Lewis et al. |
| 2010/0051266 A1* | 3/2010 | Roddy et al. ............ 166/250.01 |
| 2010/0051275 A1 | 3/2010 | Lewis et al. |
| 2010/0084132 A1 | 4/2010 | Noya et al. |
| 2010/0102986 A1 | 4/2010 | Benischek et al. |
| 2010/0148785 A1* | 6/2010 | Schaefer ................. G01V 8/02 324/338 |
| 2010/0149523 A1 | 6/2010 | Heideman et al. |
| 2010/0182600 A1 | 7/2010 | Freese et al. |
| 2010/0245096 A1 | 9/2010 | Jones et al. |
| 2010/0265509 A1 | 10/2010 | Jones et al. |
| 2010/0268470 A1 | 10/2010 | Kamal et al. |
| 2010/0269579 A1 | 10/2010 | Lawrence et al. |
| 2010/0285105 A1 | 11/2010 | Radianingtyas |
| 2010/0302539 A1 | 12/2010 | Myrick et al. |
| 2010/0326659 A1 | 12/2010 | Schultz et al. |
| 2010/0328669 A1 | 12/2010 | Myrick et al. |
| 2011/0042320 A1 | 2/2011 | Allen |
| 2011/0048708 A1 | 3/2011 | Glasbergen et al. |
| 2011/0163046 A1 | 7/2011 | Neal et al. |
| 2011/0166046 A1 | 7/2011 | Weaver et al. |
| 2011/0186290 A1 | 8/2011 | Roddy et al. |
| 2011/0197662 A1* | 8/2011 | McAlister ................. 73/61.59 |
| 2011/0212512 A1 | 9/2011 | Wang et al. |
| 2011/0312012 A1 | 12/2011 | Skinderso et al. |
| 2012/0000643 A1 | 1/2012 | Bruun et al. |
| 2012/0135396 A1 | 5/2012 | McDevitt et al. |
| 2012/0150451 A1 | 6/2012 | Skinner et al. |
| 2012/0160329 A1 | 6/2012 | MacKenzie et al. |
| 2012/0250017 A1 | 10/2012 | Morys et al. |
| 2013/0031964 A1 | 2/2013 | Tunheim et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0033701 A1 | 2/2013 | Tunheim et al. |
| 2013/0033702 A1 | 2/2013 | Tunheim et al. |
| 2013/0034842 A1 | 2/2013 | Tunheim et al. |

(56) References Cited

U.S. PATENT DOCUMENTS

| | | |
|---|---|---|
| 2014/0263974 A1 | 9/2014 | Freese et al. |
| 2014/0306096 A1 | 10/2014 | Freese et al. |
| 2015/0015884 A1 | 1/2015 | Russell et al. |
| 2015/0167456 A1 | 6/2015 | Irani |
| 2015/0212232 A1 | 7/2015 | Perkins et al. |
| 2015/0241337 A1 | 8/2015 | Talabi et al. |
| 2015/0260703 A1 | 9/2015 | Mitchell |
| 2015/0293013 A1 | 10/2015 | Tunheim et al. |
| 2015/0300945 A1 | 10/2015 | Gao et al. |
| 2015/0330215 A1 | 11/2015 | Jamison et al. |
| 2015/0346084 A1 | 12/2015 | Russell et al. |

FOREIGN PATENT DOCUMENTS

| | | |
|---|---|---|
| GB | 2353310 A | 2/2001 |
| JP | 2009284813 A | 12/2009 |
| WO | 9850680 A2 | 11/1998 |
| WO | 2004018840 A1 | 3/2004 |
| WO | 2009055200 A2 | 4/2009 |
| WO | 2009055220 A2 | 4/2009 |
| WO | 2009077758 A1 | 6/2009 |
| WO | 2010068870 A2 | 6/2010 |
| WO | 2011063086 A1 | 5/2011 |
| WO | 2013022558 A2 | 2/2013 |
| WO | 2014042909 A1 | 3/2014 |
| WO | 2014042933 A1 | 3/2014 |
| WO | 2014043010 A1 | 3/2014 |
| WO | 2014043050 A1 | 3/2014 |
| WO | 2014043057 A1 | 3/2014 |

OTHER PUBLICATIONS

Official Action for Australian Patent Application 2012294881 dated May 22, 2014.
Myrick, et al. "Spectral Tolerance Determinaton for Multivariate Optical Element Design," Fresenuis' Journal of Analytical Chemistry, 369:2001; pp. 351-355.
Gdansk et al., "A New Model for Matching Fracturing Fluid Flowback Composition," 2007 SPE Hydraulic Fracturing Technology Conference held in College Station, Texas, SPE 106040.
Gdanski et al., "Using Lines-of-Solutions to Understand Fracture Conductivity and Fracture Cleanup," SPE Production and Operations Symposium held in Oklahoma City, OK, 2011, SPE 142096.
International Search Report and Written Opinion for PCT/US2012/047065 dated Jul. 16, 2013.
International Search Report and Written Opinion for PCT/US2012/045677 dated Jul. 16, 2013.
Official Action for Canadian Patent Application No. 2,842,703 dated Jul. 25, 2014.
International Search Report and Written Opinion for PCT/US2012/047058 dated Oct. 29, 2012.
International Search Report and Written Opinion for PCT/US2013/057832 dated Nov. 22, 2013.
International Search Report and Written Opinion for PCT/US2013/058041 dated Dec. 2, 2013.
International Search Report and Written Opinion for PCT/US2013/058700 dated Dec. 6, 2013.
International Preliminary Report on Patentability for PCT/US2012/046892 dated Feb. 20, 2014.
International Search Report and Written Opinion for PCT/US2012/044148 dated Oct. 4, 2012.
International Search Report and Written Opinion for PCT/US2013/058864 dated Dec. 16, 2013.
Official Action for Australian Patent Application No. 2013252855 dated Apr. 15, 2015.
Dai et al., Molecular Factor Computing for Predictive Spectroscopy, Pharmaceutical Research, vol. 24, No. 8, 2007, pp. 1441-1449.
Mendendorp J., et al., Application of Integrated Sensing and Processing in Spectroscopic Imaging and Sensing, Journal of Chemometrics, vol. 19, 2005, pp. 533-542.
Official Action for Australian Patent Application No. 2013 252841 dated Nov. 10, 2014.
Official Action for Australian Patent Application No. 2013 252881 dated Nov. 12, 2014.
Official Action for Singapore Patent Application No. 11201500780V dated Jun. 16, 2015.
Halliburton Brochure for "Acid-on-the-Fly (AOF) Blending System," published 2009.
Official Action for Canadian Patent Application No. 2,843,518 dated Nov. 6, 2015.
Official Action for Canadian Patent Application 2,842,191 dated Dec. 17, 2015.
Official Action for Canadian Patent Application 2,879,750 dated Dec. 4, 2015.
Official Action for Canadian Patent Application 2,842,944 dated Dec. 23, 2015.
Official Action for New Zealand Patent Application No. NZ 704529 dated Jun. 9, 2015.
Official Action for Canadian Patent Application No. CA 2,842,191 dated May 6, 2015.

* cited by examiner

METHODS FOR MONITORING THE FORMATION AND TRANSPORT OF A TREATMENT FLUID USING OPTICOANALYTICAL DEVICES

BACKGROUND

The present invention generally relates to methods for the monitoring of fluids in or near real-time, and, more specifically, to methods for monitoring fluids prior to, during or after their introduction into a subterranean formation and/or to methods for monitoring produced fluids from a subterranean formation.

When conducting operations within a subterranean formation, it can be important to precisely know the characteristics of a fluid or other component present in or being introduced into the formation. Typically, the analysis of fluids and other components being introduced into a subterranean formation has been conducted off-line using laboratory analyses (e.g., spectroscopic and/or wet chemical methods). These analyses can be conducted on fluid samples being introduced into the subterranean formation or on flow back fluid samples being produced from the subterranean formation after a treatment operation has occurred. Depending on the analysis needed, such an approach can take hours to days to complete, and even in the best case scenario, a job can often be completed prior to the analysis being obtained. Furthermore, off-line laboratory analyses can sometimes be difficult to perform, require extensive sample preparation and present hazards to personnel performing the analyses. Bacterial analyses can particularly take a long time to complete, since culturing of a bacterial sample is usually needed to obtain satisfactory results.

Although off-tine, retrospective analyses can be satisfactory in certain cases, they do not generally allow real-time or near real-time, proactive control of a subterranean operation to take place. That is, off-line, retrospective analyses do not allow active control of a subterranean operation to take place, at least without significant process disruption occurring white awaiting the results of an analysis. In many subterranean operations, the lack of real-time or near real-time, proactive control can be exceedingly detrimental to the intended outcome of the subterranean operation. For example, if an incorrect treatment fluid is introduced into a subterranean formation, or if a correct treatment fluid having a desired composition but at least one undesired characteristic (e.g., the wrong concentration of a desired component, the wrong viscosity, the wrong pH, an interfering impurity, a wrong sag potential, the wrong kind or concentration of proppant particulates, bacterial contamination and/or the like) is introduced into a subterranean formation, the subterranean operation can produce an ineffective outcome or a less effective outcome than desired. Worse yet, if an incorrect treatment fluid or a treatment fluid having an undesired characteristic is introduced into the subterranean formation, damage to the formation can occur in some cases. Such damage can sometimes result in the abandonment of a wellbore penetrating the subterranean formation, or a remediation operation can sometimes be needed to at least partially repair the damage. In either case, the consequences of introducing the wrong treatment fluid into a subterranean formation can have serious financial implications and result in considerable production delays.

Off-line, retrospective analyses can also be unsatisfactory for determining the true suitability of a treatment fluid for performing a treatment operation or for evaluating the true effectiveness of a treatment operation. Specifically, once removed from their subterranean environment and transported to a laboratory, the characteristics of a treatment fluid sample can change, thereby making the properties of the sample non-indicative of the true effect produced by the treatment fluid in the subterranean formation. Similar issues also can be encountered in the analysis of treatment fluids before they are introduced into a subterranean formation. That is, the properties of the treatment fluid can change during the lag time between collection and analysis. In such cases, a treatment fluid that appears unsuitable for subterranean use based upon its laboratory analysis could have been suitable if introduced into the subterranean formation at an earlier time. The converse can also be true. Factors that can alter the characteristics of a treatment fluid during the lag time between collection and analysis can include, for example, scaling, reaction of various components in the fluid with one another, reaction of various components in the fluid with components of the surrounding environment, simple chemical degradation, and bacterial growth.

In addition, the monitoring of source materials that are being used in the formation of a treatment fluid can also be of interest. For example, if an incorrect source material or the wrong quality and/or quantity of a source material is used to form a treatment fluid, it is highly likely that the treatment fluid will have an undesired characteristic. In this regard, monitoring of a source material can also be an important quality control feature in the formation of a treatment fluid.

In addition to monitoring the characteristics of treatment fluids that are being introduced into a subterranean formation, the monitoring of fluids produced from a subterranean formation can also be of considerable interest. Produced fluids of interest can include both native formation fluids and flow back fluids produced after the completion of a treatment operation. As noted previously, the characteristics of a flow back fluid can provide an indication of the effectiveness of treatment operation, if analyzed properly. In spite of the wealth of chemical information that can be present in these fluids, it has sometimes been conventional in the art to simply dispose of produced formation water or flow back fluids resulting from a treatment operation. As an added concern, the significant volumes of fluids produced from a subterranean formation can present enormous waste disposal issues, particularly in view of increasingly strict environmental regulations regarding the disposal of produced water and other types of waste water. The inability to rapidly analyze produced fluids can make the recycling or disposal of these fluids exceedingly problematic, since they must be stored until analyses can be completed. As previously indicated, even when an analysis has been completed, there is no guarantee that the sample will remain indicative of the produced bulk fluid.

More generally, the monitoring of fluids in or near real-time can be of considerable interest in order to monitor how the fluids are changing with time, thereby serving as a quality control measure for processes in which fluids are used. Specifically, issues such as, for example, scaling, impurity buildup, bacterial growth and the like can impede processes in which fluids are used, and even damage process equipment in certain cases, For example, water streams used in cooling towers and like processes can become highly corrosive over time and become susceptible to scale formation and bacterial growth. Corrosion and scale formation can damage pipelines through which the water is flowing and potentially lead to system breakdowns. Similar issues can be encountered for fluids subjected to other types of environments.

Spectroscopic techniques for measuring various characteristics of materials are well known and are routinely used under laboratory conditions. In some cases, these spectroscopic techniques can be carried out without using an involved sample preparation. It is more common, however, to carry out various sample preparation steps before conducting the analysis. Reasons for conducting sample preparation steps can include, for example, removing interfering background materials from the analyte of interest, converting the analyte of interest into a chemical form that can be better detected by the chosen spectroscopic technique, and adding standards to improve the accuracy of quantitative measurements. Thus, there can be a delay in obtaining an analysis due to sample preparation time, even discounting the transit time of the sample to a laboratory. Although spectroscopic techniques can, at least in principle, be conducted at a job site or in a process, the foregoing concerns regarding sample preparation times can still apply. Furthermore, the transitioning of spectroscopic instruments from a laboratory into a field or process environment can be expensive and complex. Reasons for these issues can include, for example, the need to overcome inconsistent temperature, humidity and vibration encountered during field or process use. Furthermore, sample preparation, when required, can be difficult under field analysis conditions. The difficulty of performing sample preparation in the field can be especially problematic in the presence of interfering materials, which can further complicate conventional spectroscopic analyses, Quantitative spectroscopic measurements can be particularly challenging in both field and laboratory settings due to the need for precision and accuracy in sample preparation and spectral interpretation.

SUMMARY OF THE INVENTION

The present invention generally relates to methods for the monitoring of fluids in or near real-time, and, more specifically, to methods for monitoring fluids prior to, during or after their introduction into a subterranean formation and/or to methods for monitoring produced fluids from a subterranean formation.

In one embodiment, the present invention provides a method comprising: providing at least one source material; combining the at least one source material with a base fluid to form a treatment fluid; and monitoring a characteristic of the treatment fluid using a first opticoanalytical device that is in optical communication with a flow pathway for transporting the treatment fluid.

In one embodiment, the present invention provides a method comprising: preparing a treatment fluid; transporting the treatment fluid to a job site; introducing the treatment fluid into a subterranean formation at the jobsite; monitoring a characteristic of the treatment fluid at the job site using a first opticoanalytical device that is in optical communication with a flow pathway for transporting the treatment fluid; determining if the characteristic of the treatment fluid being monitored using the first opticoanalytical device makes the treatment fluid suitable for being introduced into the subterranean formation; and optionally, adjusting the characteristic of the treatment fluid.

In one embodiment, the present invention provides a method comprising: forming a treatment fluid on-the-fly by adding at least one component to a base fluid stream; introducing the treatment fluid into a subterranean formation; and monitoring a characteristic of the treatment fluid using an opticoanalytical device while the treatment fluid is being introduced into the subterranean formation.

In one embodiment, the present invention provides a method comprising: providing at least one acid; combining the at least one acid with a base fluid to form an acidizing fluid; and monitoring a characteristic of the acidizing fluid using a first opticoanalytical device that is in optical communication with a flow pathway for transporting the acidizing fluid.

In one embodiment, the present invention provides a method comprising: providing an acidizing fluid comprising at least one acid; introducing the acidizing fluid into a subterranean formation; and monitoring a characteristic of the acidizing fluid using a first opticoanalytical device that is in optical communication with a flow pathway for transporting the acidizing fluid.

In one embodiment, the present invention provides a method comprising: forming an acidizing fluid on-the-fly by adding at least one acid to a base fluid stream; introducing the acidizing fluid into a subterranean formation; and monitoring a characteristic of the acidizing fluid using an opticoanalytical device while the acidizing fluid is being introduced. into the subterranean formation, In one embodiment, the present invention provides a method comprising: providing at least one fracturing fluid component; combining the at least one fracturing fluid component with a base fluid to form a fracturing fluid; and monitoring a characteristic of the fracturing fluid using a first opticoanalytical device that is in optical communication with a flow pathway for transporting the fracturing fluid.

In one embodiment, the present invention provides a method comprising: providing a fracturing fluid comprising at least one fracturing fluid component; introducing the fracturing fluid into a subterranean formation at a pressure sufficient to create or enhance at least one fracture therein; and monitoring a characteristic of the fracturing fluid using a first opticoanalytical device that is in optical communication with a flow pathway for transporting the fracturing fluid.

In one embodiment, the present invention provides a method comprising: forming a fracturing fluid on-the-fly by adding at least one fracturing fluid component to a base fluid stream; introducing the fracturing fluid into a subterranean formation at a pressure sufficient to create or enhance at least one fracture therein; and monitoring a characteristic of the fracturing fluid using an opticoanalytical device while the fracturing fluid is being introduced into the subterranean formation.

In one embodiment, the present invention provides a method comprising: providing a treatment fluid comprising a base fluid and at least one additional component; introducing the treatment fluid into a subterranean formation; allowing the treatment fluid to perform a treatment operation in the subterranean formation; and monitoring a characteristic of the treatment fluid or a formation fluid using at least a first opticoanalytical device within the subterranean formation, during a flow back of the treatment fluid produced from the subterranean formation, or both.

In one embodiment, the present invention provides a method comprising: providing a treatment fluid comprising a base fluid and at least one additional component; introducing the treatment fluid into a subterranean formation; and monitoring a characteristic of the treatment fluid using at least a first opticoanalytical device that is in optical communication with a flow pathway for transporting the treatment fluid before the treatment fluid is introduced into the subterranean formation, In one embodiment, the present invention provides a method comprising: providing an acidizing fluid comprising a base fluid and at least one acid; introducing the acidizing fluid into a subterranean formation; allowing the acidizing fluid to perform an acidizing operation in the subterranean formation; and monitoring a characteristic of the acidizing fluid or a formation fluid using at least a first opticoanalytical device within the subterranean formation, during a flow back of the acidizing fluid produced from the subterranean formation, or both.

In one embodiment, the present invention provides a method comprising: providing an acidizing fluid comprising a base fluid and at least one acid; introducing the acidizing fluid into a subterranean formation; and monitoring a characteristic of the acidizing fluid using at least a first opticoanalytical device that is in optical communication with a flow pathway for transporting the acidizing fluid before the acidizing fluid is introduced into the subterranean formation.

In one embodiment, the present invention provides a method comprising: providing a fracturing fluid comprising a base fluid and at least one fracturing fluid component; introducing the fracturing fluid into a subterranean formation at a pressure sufficient to create or enhance at least one fracture therein, thereby performing a fracturing operation in the subterranean formation; and monitoring a characteristic of the fracturing fluid or a formation fluid using at least a first opticoanalytical device within the subterranean formation, during a flow back of the fracturing fluid produced from the subterranean formation, or both.

In one embodiment, the present invention provides a method comprising: providing a fracturing fluid comprising a base fluid and at least one fracturing fluid component; introducing the fracturing fluid into a subterranean formation at a pressure sufficient to create or enhance at least one fracture therein; and monitoring a characteristic of the fracturing fluid using at least a first opticoanalytical device that is in optical communication with a flow pathway for transporting the fracturing fluid before the fracturing fluid is introduced into the subterranean formation.

In one embodiment, the present invention provides a method comprising: providing water from a water source; monitoring a characteristic of the water using a first opticoanalytical device that is in optical communication with a flow pathway for transporting the water; and introducing the water into a subterranean formation.

In one embodiment, the present invention provides a method comprising: producing water from a first subterranean formation, thereby forming a produced water; monitoring a characteristic of the produced water using a first opticoanalytical device that is in optical communication with a flow pathway for transporting the produced water; forming a treatment fluid comprising the produced water and at least one additional component; and introducing the treatment fluid into the first subterranean formation or a second subterranean formation.

In one embodiment, the present invention provides a method comprising: providing water from a water source; monitoring a characteristic of the water using a first opticoanalytical device that is in optical communication with a flow pathway for transporting the water; and treating the water so as to alter at least one property thereof in response to the characteristic of the water monitored using the first opticoanalytical device.

In one embodiment, the present invention provides a method comprising: providing a fluid in a fluid stream; and monitoring a characteristic of the fluid using a first opticoanalytical device that is in optical communication with the fluid in the fluid stream.

In one embodiment, the present invention provides a method comprising: providing a fluid in a fluid stream; monitoring a characteristic of the fluid using a first opticoanalytical device that is in optical communication with the fluid in the fluid stream; determining if the characteristic of the fluid needs to be adjusted based upon an output from the first opticoanalytical device; performing an action on the fluid in the fluid stream so as to adjust the characteristic thereof; and after performing the action on the fluid in the fluid stream, monitoring the characteristic of the fluid using a second opticoanalytical device that is in optical communication with the fluid in the fluid stream.

In one embodiment, the present invention provides a method comprising: providing water in a fluid stream; performing an action on the water in the fluid stream so as to adjust a characteristic of the water; after performing the action on the water in the fluid stream, monitoring the characteristic of the water using an opticoanalytical device that is in optical communication with the water in the fluid stream; and determining if the characteristic of the water lies within a desired range.

In one embodiment, the present invention provides a method comprising: monitoring live bacteria in water using a first opticoanalytical device that is in optical communication with the water.

In one embodiment, the present invention provides a method comprising: providing a treatment fluid comprising a base fluid and at least one additional component; monitoring live bacteria in the treatment fluid using at least a first opticoanalytical device that is in optical communication with a flow pathway for transporting the treatment fluid; and introducing the treatment fluid into a subterranean formation, after monitoring the live bacteria therein.

In one embodiment, the present invention provides a method comprising: providing a treatment fluid comprising a base fluid and at least one additional component; introducing the treatment fluid into a subterranean formation; and monitoring live bacteria in the treatment fluid within the subterranean formation using an opticoanalytical device located therein.

The features and advantages of the present invention will be readily apparent to one having ordinary skill in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to one having ordinary skill in the art and having the benefit of this disclosure.

DETAILED DESCRIPTION

Figure 1:
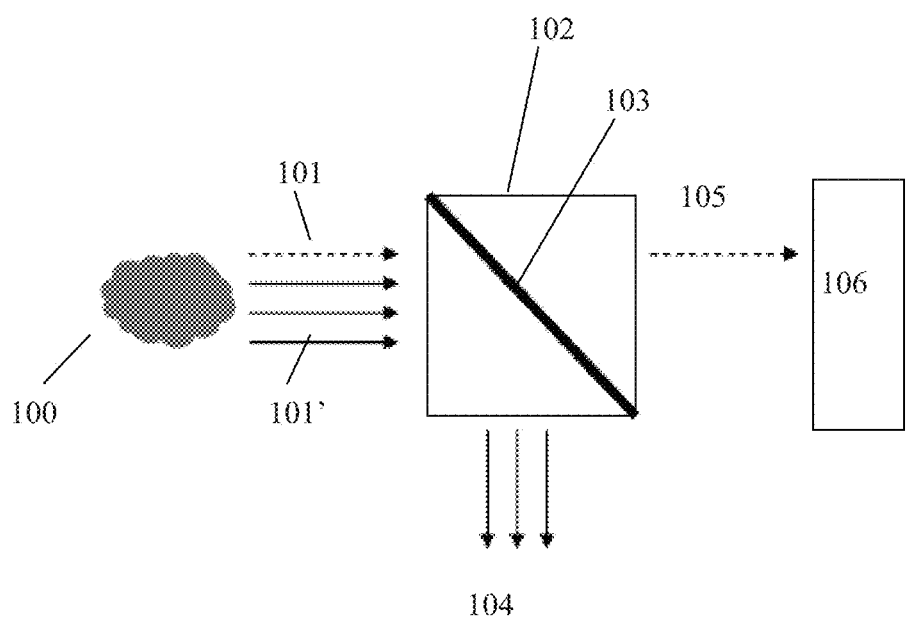
FIG. 1 shows a block diagram non-mechanistically illustrating how an optical computing device separates electromagnetic radiation related to a characteristic or analyte of interest from other electromagnetic radiation.

The present invention generally relates to methods for the monitoring of fluids in or near real-time, and, more specifically, to methods for monitoring fluids prior to, during or after their introduction into a subterranean formation and/or to methods for monitoring produced fluids from a subterranean formation.

Various embodiments described herein utilize opticoanalytical devices that can be utilized for the real-time or near real-time monitoring of fluids that are ultimately introduced into a subterranean formation, Likewise, these opticoanalytical devices can be used to monitor fluids that are produced from a subterranean formation (including both flow back fluids, formation fluids, and combinations thereof) or to monitor and regulate fluids that are used in various processes. These devices, which are described in more detail herein, can advantageously provide a measure of real-time or near real-time quality control over the introduction of fluids into a subterranean formation that cannot presently be achieved with either onsite analyses at a job site or more detailed analyses that take place in a laboratory. Further, these devices can advantageously provide timely information regarding the effectiveness of a treatment operation being performed in a subterranean formation or the monitoring of a fluid in a fluid stream, particularly while the fluid stream is being modified in some way. A significant advantage of these devices is that they can be configured to specifically detect and/or measure a particular component of a fluid, thereby allowing qualitative and/or quantitative analyses of the fluid to occur without sample processing taking place. The ability to perform quantitative analyses in real-time or near real-time represents a distinct advantage over time-consuming laboratory analyses, which can either delay the start of a subterranean operation or provide information too late to proactively guide the performance of a subterranean operation. In addition, the opticoanalytical devices can be capable of monitoring a treatment operation while a treatment fluid resides within a subterranean formation.

The opticoanalytical devices utilized in the embodiments described herein can advantageously allow at least some measure of proactive or responsive control over a treatment operation or other type of operation using a fluid to take place. In this regard, the capability of real-time or near real-time monitoring using the opticoanalytical devices can advantageously allow automation of a treatment operation to take place through an active feedback of information obtained using the opticoanalytical devices. Specifically, by coupling the opticoanalytical device to a processor configured for manipulating analytical data obtained therefrom (e.g., a computer, an artificial neural network, and/or the like), a treatment operation can be proactively controlled to allow a more effective treatment operation to take place. In some cases, the analytical data obtained from the opticoanalytical device can be manipulated to determine ways in which a fluid can be modified to produce or enhance a desired characteristic.

In addition, real-time or near real-dine monitoring using opticoanalytical devices according to the embodiments described herein can enable the collection and archival of fluid information in conjunction with operational information to optimize subsequent subterranean operations in the same formation or in a different formation having similar chemical and physical characteristics. Significantly, real-time or near real-time monitoring using opticoanalytical devices can enhance the capacity for remote job execution.

The opticoanalytical devices suitable fix use in the present embodiments can be deployed at any of a number of various points throughout a system for performing a treatment operation in a subterranean formation. Depending on the point(s) at which a treatment operation is monitored using the opticoanalytical device(s), various types of information about the treatment operation can be obtained. For example, in some cases, quality control information regarding source materials and treatment fluids formed therefrom can be obtained. In some cases, the change in a treatment fluid before and after introduction into a subterranean formation can be obtained. In addition, the opticoanalytical devices of the present embodiments can be used to monitor a treatment fluid of a formation fluid while it is downhole and subject to conditions of the subterranean environment, where it can potentially interact with the surface of a subterranean formation. Still further, the opticoanalytical devices can be used to monitor a fluid being produced from a subterranean formation. Characterization of the produced fluid can provide information about the effectiveness of a treatment operation that has taken place. In addition, characterization of the produced fluid can more readily allow disposal or recycling of the fluid to take place, if that is desired. It is to be recognized that the foregoing listing of information that can be obtained using opticoanalytical devices to monitor and/or control a treatment and/or production process should be considered illustrative in nature only. Depending on the locations of the opticoartalytical devices and the processing of information obtained. therefrom, other types of information can be obtained as well.

Even more generally, the opticoanalytical devices can be used to monitor fluids and various changes thereto according to the embodiments described herein. In some cases, the opticoanalytical devices can be used to monitor changes to a fluid that take place over time, for example, in a pipeline or storage vessel. In some cases, the opticoanalytical devices can be used to monitor changes to a fluid that take place as a result of performing an action on the fluid (e.g., adding a component thereto, removing a component therefrom, or exposing the fluid. to a condition that potentially changes a characteristic of the fluid in some way). Thus, the opticoanalytical devices can be used to monitor processes that take place upon fluids and in which fluids are used to gain an additional measure of process control.

As used herein, the term "fluid" refers to a substance that is capable of flowing, including particulate solids, liquids, and gases. In some embodiments, the fluid can be an aqueous fluid, including water. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquid and/or gases. illustrative gases that can be considered fluids according to the present embodiments include, for example, air, nitrogen, carbon dioxide, argon, methane and other hydrocarbon gases, and/or the like.

As used herein, the term "treatment fluid" refers to a fluid that is placed in a subterranean formation in order to perform a desired function. Treatment fluids can be used in a variety of subterranean operations, including, but not limited to, drilling operations, production treatments, stimulation treatments, remedial treatments, fluid diversion operations, fracturing operations, and the like. As used herein, the terms "treatment" and "treating," as they refer to subterranean operations, refer to any subterranean operation that uses a fluid in conjunction with performing a desired function and/or achieving a desired purpose. The terms "treatment" and "treating," as used herein, do not imply any particular action by the fluid or any particular component thereof unless otherwise specified. Treatment fluids can include, for example, drilling fluids, fracturing fluids, acidizing fluids, conformance treatment fluids, diverting fluids, damage control fluids, remediation fluids, scale removal and inhibition fluids, chemical floods, sand control fluids, and the like. Generally, any treatment fluid and any treatment operation can be monitored according to the general techniques described herein.

As used herein, the term "characteristic" refers to a chemical or physical property of a substance. Illustrative characteristics of a substance that can be monitored according to the methods described herein can include, for example, chemical composition (identity and concentration, in total or of individual components), impurity content, pH, viscosity, density, ionic strength, total dissolved solids, salt content, porosity, opacity, bacteria content, and the like.

As used herein, the term "electromagnetic radiation" refers to radio waves, microwave radiation, infrared and near-infrared radiation, visible light, ultraviolet light, X-ray radiation and gamma ray radiation.

As used herein, the term "in-process" refers to an event that takes place while a treatment fluid is being introduced into a subterranean formation to perform a treatment operation, while the treatment operation is occurring, or while a flow back fluid is being produced from the subterranean formation as a result of the treatment operation.

As used herein, the term "flow back fluid" refers to a treatment fluid that is produced from a subterranean formation subsequent to a treatment operation.

As used herein, the term "produced fluid" refers to a fluid that is obtained from a subterranean formation. A produced fluid can include a flow back fluid, a native formation fluid present in the subterranean formation (including formation water or oil), or a combination thereof.

As used herein, the term "formation fluid" refers to a fluid that is natively present in a subterranean formation.

As used herein, the term "in-line" refers to an event that takes place during a process without the process being substantially disrupted.

As used herein, the term "opticoanalytical device" refers to an optical device that is operable to receive an input of electromagnetic radiation from a substance and produce an output of electromagnetic radiation from a processing element that is changed in some way so as to be readable by a detector, such that an output of the detector can be correlated to at least one characteristic of the substance. The output of electromagnetic radiation from the processing element can be reflected electromagnetic radiation and/or transmitted electromagnetic radiation, and whether reflected or transmitted electromagnetic radiation is analyzed by the detector will be a matter of routine experimental design. In addition, fluorescent emission of the substance can also be monitored by the optical devices.

As used herein, the term "flow pathway" refers to a route through which a fluid is capable of being transported between two points. Flow pathways between two points need not necessarily be continuous. Illustrative flow pathways can include, various transportation means such as, for example, pipelines, hoses, tankers, railway tank cars, barges, ships, and the like. In addition, the term flow pathway should not be construed to mean that a fluid therein is flowing, rather that a fluid therein is capable of being transported through flowing.

As used herein, the term "fluid stream" refers to quantity of fluid that is flowing, for example, in a hose, pipeline or spray.

As used herein, the term "kill ratio" refers to the number of live bacteria present in a sample after a bactericidal treatment relative to the number of live bacteria present in a sample before a bactericidal treatment.

As used herein, the term "live bacteria" refers to bacteria that are capable of metabolic activity and normal reproduction. In some cases, live bacteria can be metabolically inactive and not in a state of normal reproduction due to exposure to certain environmental conditions (e.g., temperature or lack of an appropriate nutrient source), while still retaining the capability for normal metabolic activity and reproduction upon exposure to more favorable environmental conditions. In some embodiments, live bacteria can be part of a population of bacteria that has been substantially unaffected by a bactericidal treatment. More specifically, the term "live bacteria" refers to bacteria whose DNA or RNA has not been modified or degraded by a bactericidal treatment or whose cell wall structure has not been modified or degraded by a bactericidal treatment.

Opticoanalytical Devices

In general, opticoanalytical devices suitable for use in the present embodiments can contain a processing element and a detector. In some embodiments, the opticoanalytical devices can be configured for specifically detecting and analyzing a characteristic or substance of interest. In some embodiments, the opticoanalytical devices can be configured to quantitatively measure a characteristic or a substance of interest. In other embodiments, the opticoanalytical devices can be general purpose optical devices, with post-acquisition processing (e.g., through computer means) being used to specifically detect a characteristic or substance of interest.

In some embodiments, suitable opticoanalytical devices can be an optical computing device. Suitable optical computing devices are described in commonly owned U.S. Pat. Nos. 6,198,531; 6,529,276; 7,123,844; 1,834,999; 7,911,605, and 7,920,258, each of which is incorporated herein by reference in its entirety, and U.S. patent applications Ser. No. 12/094,460 (U.S. Patent Application Publication 2009/0219538), 12/094,465 (U.S. Patent Application Publication 2009/0219539), and 12/094,469 (U.S. Patent Application Publication 2009/0073433), each of which is also incorporated herein by reference in its entirety. Accordingly, these optical computing devices will only be described in brief herein. Other types of optical computing devices can also be suitable in alternative embodiments, and the foregoing optical computing devices should not be considered to be limiting.

Optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for sample processing. in this regard, the optical computing devices can be specifically configured (trained) to detect and analyze particular characteristics and/or substances (analytes) of interest by using samples having known compositions and/or characteristics. As a result, interfering signals can be discriminated from those of interest in a sample by appropriate configuration of the optical computing devices, such that the optical computing devices can provide a rapid response regarding the characteristics of a substance based on the detected output. In some embodiments, the detected output can be converted into a voltage that is distinctive of the magnitude of a characteristic being monitored in the sample. The foregoing advantages and others make the optical computing devices particularly well suited for field and downhole use.

Unlike conventional spectrometers, the optical computing devices can be configured to detect not only the composition and concentrations of a material or mixture of materials, but they also can be configured to determine physical properties and other characteristics of the material as well, based on their analysis of the electromagnetic radiation. received from the sample. For example, the optical computing devices can be configured to determine the concentration of an analyte and correlate the determined concentration to a characteristic of a substance by using suitable processing means. The optical computing devices can be configured to detect as many characteristics or analytes as desired in a sample. All that is required to accomplish the monitoring of multiple characteristics or analytes is the incorporation of suitable processing and detection means within the optical computing device or each characteristic or analyte. The properties of a substance can be a combination of the properties of the analytes therein (e.g., a linear combination). Accordingly, the more characteristics and analytes that are detected and analyzed using the optical computing device, the more accurately the properties of a substance can be determined.

Fundamentally, optical computing devices utilize electromagnetic radiation to perform calculations, as opposed to the hardwired circuits of conventional electronic processors. When electromagnetic radiation interacts with a substance, unique physical and chemical information about the substance are encoded in the electromagnetic radiation that is reflected from, transmitted through or radiated from the sample. This information is often referred to as the substance's spectral "fingerprint." The optical computing devices utilized herein are capable of extracting the information of the spectral fingerprint of multiple characteristics or analytes within a substance and converting that information into a detectable output regarding the overall properties of a sample. That is, through suitable configuration of the optical computing devices, electromagnetic radiation associated with characteristics or analytes of interest in a substance can be separated from electromagnetic radiation associated with all other components of a sample in order to estimate the sample's properties in real-time or near real-time.

In various embodiments, the optical computing devices can contain an integrated computational element (ICE) that is capable of separating electromagnetic radiation related to the characteristic or analyte of interest from electromagnetic radiation related to other components of a sample. Further details regarding how the optical computing devices can separate and process electromagnetic radiation related to the characteristic Or analyte of interest are described in U.S. Pat. No. 7,920,258, previously incorporated herein by reference. FIG. 1 shows a block diagram non-mechanistically illustrating how an optical computing device separates electromagnetic radiation related to a characteristic or analyte of interest from other electromagnetic radiation. As shown in FIG. 1, after being illuminated with incident electromagnetic radiation, sample 100 containing an analyte of interest produces an output of electromagnetic radiation, some of which is electromagnetic radiation 101 from the characteristic or analyte of interest and some of which is background electromagnetic radiation 101' from other components of sample 100. Electromagnetic radiation 101 and 101' impinge upon optical computing device 102, which contains ICE 103 therein. ICE 103 separates electromagnetic radiation 101 from electromagnetic radiation 101'. Transmitted electromagnetic radiation 105, which is related to the characteristic or analyte of interest, is carried to detector 106 for analysis and quantification (e.g., to produce an output of the characteristics of sample 100). Reflected electromagnetic radiation 104, which is related to other components of sample 100, can be directed away from detector 106. In alternative configurations of optical computing device 102, reflected electromagnetic radiation 104 can be related to the analyte of interest, and transmitted. electromagnetic radiation 105 can be related to other components of the sample. In some embodiments, a second detector (not shown) can be present that detects the electromagnetic radiation reflected from ICE 103. Without limitation, the output of the second detector can be used to normalize the output of detector 106. In some embodiments, a beam splitter can be employed (not shown) to split the two optical beams, and the transmitted or reflected electromagnetic radiation can then directed to ICE 103. That is, in such embodiments, ICE 103 does not function as the beam splitter, as depicted in FIG. 1, and the transmitted or reflected electromagnetic radiation simply passes through ICE 103, being computationally processed therein, before travelling to detector 106.

Suitable ICE components are described in commonly owned U.S. Pat. Nos. 6,198,531; 6,529276; and 7,911,605, each previously incorporated herein by reference, and in Myrick, et al. "Spectral tolerance determination for multivariate optical element design," FRESENUIS' JOURNAL OF ANALYTICAL. CHEMISTRY, 369:2001, pp. 351-355, which is also incorporated herein by reference in its entirety. In general, an ICE comprises an optical element whose transmissive, reflective, and/or absorptive properties are suitable for detection of a characteristic or analyte of interest. The optical element can contain a specific material for accomplishing this purpose (e.g., silicon, germanium, water, or other material of interest). In some embodiments, the material can be doped or two or more materials can be combined in a. manner to result in the desired optical characteristic. For example, deposited layers of materials that have appropriate concentrations and thicknesses can be used to create an ICE having suitable properties. In addition to solids, an ICE can also contain liquids and/or gases, optionally in combination with solids, in order to produce a desired optical characteristic. In the case of gases and liquids, the ICE can contain a vessel which houses the gases or liquids. In addition to the foregoing, an ICE can also comprise holographic optical elements, gratings, and/or acousto-optic elements, for example, that can create transmission, reflection, and/or absorptive properties of interest. Other types of ICE components can also be suitable in alternative embodiments, and the foregoing ICE components should not be considered to be limiting.

Once ICE, 103 has separated electromagnetic radiation 101 related to the sample, optical computing device 102 can provide an optical signal (e.g., transmitted electromagnetic radiation 105), which is related to the amount (e.g., concentration) of the characteristic or analyte of interest. In some embodiments, the relation between the optical signal and the concentration can be a direct proportion. Detector 106 can be configured to detect transmitted electromagnetic radiation 105 and produce voltage output in an embodiment, which is related to the amount of the characteristic or analyte of interest.

When monitoring more than one analyte at a time, various configurations for multiple ICEs can be used, where each ICE has been configured to detect a particular characteristic or analyte of interest. In some embodiments, the characteristic or analyte can be analyzed sequentially using multiple ICEs that are presented to a single beam of electromagnetic radiation being reflected from or transmitted through a sample. In some embodiments, multiple ICEs can be located on a rotating disc, where the individual ICEs are only exposed to the beam of electromagnetic radiation for a short time. Advantages of this approach can include the ability to analyze multiple analytes using a single optical computing device and the opportunity to assay additional analytes simply by adding additional ICEs to the rotating disc. In various embodiments, the rotating disc can be turned at a frequency of about 10 RPM to about 30,000 RPM such that each analyte in a sample is measured rapidly. In some embodiments, these values can be averaged over an appropriate time domain (e.g., about 1 millisecond to about 1 hour) to more accurately determine the sample characteristics.

In other embodiments, multiple optical computing devices can be placed parallel, where each optical computing device contains a unique ICE that is configured to detect a particular characteristic or analyte of interest. In such embodiments, abeam splitter can divert a portion of the electromagnetic radiation being reflected by, emitted from or transmitted through from the substance being analyzed into each optical computing device. Each optical computing device, in turn, can be coupled to a detector or detector array that is configured to detect and analyze an output of electromagnetic radiation from the optical computing device. Parallel configurations of optical computing devices can be particularly beneficial for applications that require low power inputs and/or no moving parts.

In still additional embodiments, multiple optical computing devices can be placed in series, such that characteristics or analytes are measured sequentially at different locations and times. For example, in some embodiments, a characteristic or analyte can be measured in a first location using a first optical computing device, and the characteristic or analyte can be measured in a second location using a second optical computing device. In other embodiments, a first characteristic or analyte can be measured in a first location using a first optical computing device, and a second characteristic or analyte can be measured in a second location using a second optical computing device. It should also be recognized that any of the foregoing configurations for the optical computing devices can be used in combination with a series configuration in any of the present embodiments. For example, two optical computing devices having a rotating disc with a plurality of ICEs thereon can be placed in series for performing an analysis. Likewise, multiple detection stations, each containing optical computing devices in parallel, can be placed in series for performing an analysis.

In alternative embodiments, a suitable opticoanalytical device can be a spectrometer than has been ruggedized for field use. In various embodiments, a suitable spectrometer can include, for example, an infrared spectrometer, a UV/VIS spectrometer, a Raman spectrometer, a microwave spectrometer, a fluorescence spectrometer, and the like. It is to be recognized that any of the preferred embodiments described herein using an optical computing device can be practiced in a like manner using a spectrometer, which in most cases has been ruggedized for field use. Techniques for ruggedizing the foregoing spectrometers will be dependent upon the field conditions in which measurements are to take place. Suitable ruggedization techniques will be apparent to one having ordinary skill in the art.

Automated Control and Remote Operation

In some embodiments, the characteristics of the sample being analyzed. using the opticoanalytical device can be further processed computationally to provide additional characterization information about the substance being analyzed. In some embodiments, the identification and concentration of each analyte in a sample can be used to predict certain physical characteristics of the sample. For example, the bulk characteristics of a sample can be estimated by using a combination of the properties conferred to the sample by each analyte.

In some embodiments, the concentration of each analyte or the magnitude of each characteristic determined using the opticoanalytical devices can be fed into an algorithm operating under computer control. In some embodiments, this algorithm can make predictions on how the characteristics of the sample change if the concentrations of the analytes are changed relative to one another. In some embodiments, the algorithm can be linked to any step of the process for introducing a fluid or producing a fluid from a subterranean formation so as to change the characteristics of the fluid being introduced to or produced from a subterranean formation. In more general embodiments, the algorithm can be linked to a fluid being modified by some process, such that the fluid can be monitored in-process. In some embodiments, the algorithm can simply produce an output that is readable by an operator, and the operator can manually take appropriate action based upon the output. For example, if the algorithm determines that a component of a treatment fluid being introduced into a subterranean formation is out of range, the operator can direct that additional amounts of the component be added to the treatment fluid "on-the-fly." In some embodiments, onsite monitoring control by the operator can take place, while in other embodiments the operator can be offsite while controlling the process remotely through suitable communication means. In some embodiments, the algorithm can take proactive process control by automatically adjusting the characteristics of a treatment fluid being introduced into a subterranean formation or by halting the introduction of the treatment fluid in response to an out of range condition. For example, the algorithm can be configured such that if a component of interest is out of range, the amount of the component can be automatically increased or decreased in response. In some embodiments, the response to the out of range condition can involve the addition of a component that is not already in the treatment fluid. Likewise, if an inappropriate analyte is detected in a fluid to be introduced into a subterranean formation, the algorithm can determine a corrective action (e.g., a component to be added) to counteract or remove the characteristics conferred by that analyte.

In some embodiments, the algorithm can be part of an artificial neural network. In some embodiments, the artificial neural network can use the concentration of each detected analyte in order to evaluate the characteristics of the sample and predict how to modify the sample in order to alter its properties in a desired way. Illustrative but non-limiting artificial neural networks are described in commonly owned U.S. patent application Ser. No. 11/986,763 (U.S. Patent Application Publication 2009/0182693), which is incorporated herein by reference in its entirety. For example, in a fluid containing two analytes of interest, a simple algorithm-based approach might detect that the concentrations of both analytes are out of range and adjust the composition of the fluid to bring the analytes back in range. However, an adjustment using an artificial neural network might determine that even though both analytes are out of range, the detected amounts, in combination, maintain a bulk characteristic of the fluid within a desired range. For example, an algorithm-based approach might determine that both a gelling agent concentration and ionic strength are out of their specified range for a fluid and mandate adjustment thereof;

however, an artificial neural network might determine that the analyzed. concentrations, in combination, are sufficient for maintaining a desired viscosity within the fluid and not direct that adjustment be made. Any combination of analytes and properties determined thereby lie within the spirit and scope of the present invention.

It is to be recognized that an artificial neural network can be trained using samples having known concentrations, compositions and properties. As the training set of information available to the artificial neural network becomes larger, the neural network can become more capable of accurately predicting the characteristics of a sample having any number of analytes present therein. Furthermore, with sufficient training, the artificial neural network can more accurately predict the characteristics of the sample, even in the presence of unknown analytes.

It is to be recognized that in the various embodiments herein directed to computer control and artificial neural networks that various blocks, modules, elements, components, methods and algorithms can be implemented through using computer hardware, software and combinations thereof. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the spirit and scope of the embodiments expressly described.

Computer hardware used to implement the various illustrative blocks, modules, elements, components, methods and algorithms described herein can include a processor configured to execute one or more sequences of instructions, programming or code stored on a readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network or any like suitable entity that can perform calculations or other manipulations of data In some embodiments, computer hardware can further include elements such as, for example, a memory [e.g., random access memory (RAM), flash memory, read only memory (ROM), programmable read only memory (PROM), erasable PROM], registers, hard disks, removable disks, CD-ROMS, DVDs, or any other like suitable storage device.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and software.

As used herein, a machine-readable medium will refer to any medium that directly or indirectly provides instructions to a processor for execution. A. machine-readable medium can take on many forms including, for example, non-volatile media, volatile media, and transmission media. Non-volatile media can include, for example, optical and magnetic disks, Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the opticoanalytical devices can be archived along with data associated with operational parameters being logged at a job site. Evaluation of job performance can then be assessed and improved for future operations or such information can be used to design subsequent operations. In addition, the data and information can be communicated to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Location of the Opticoanalytical devices

Figure 2:
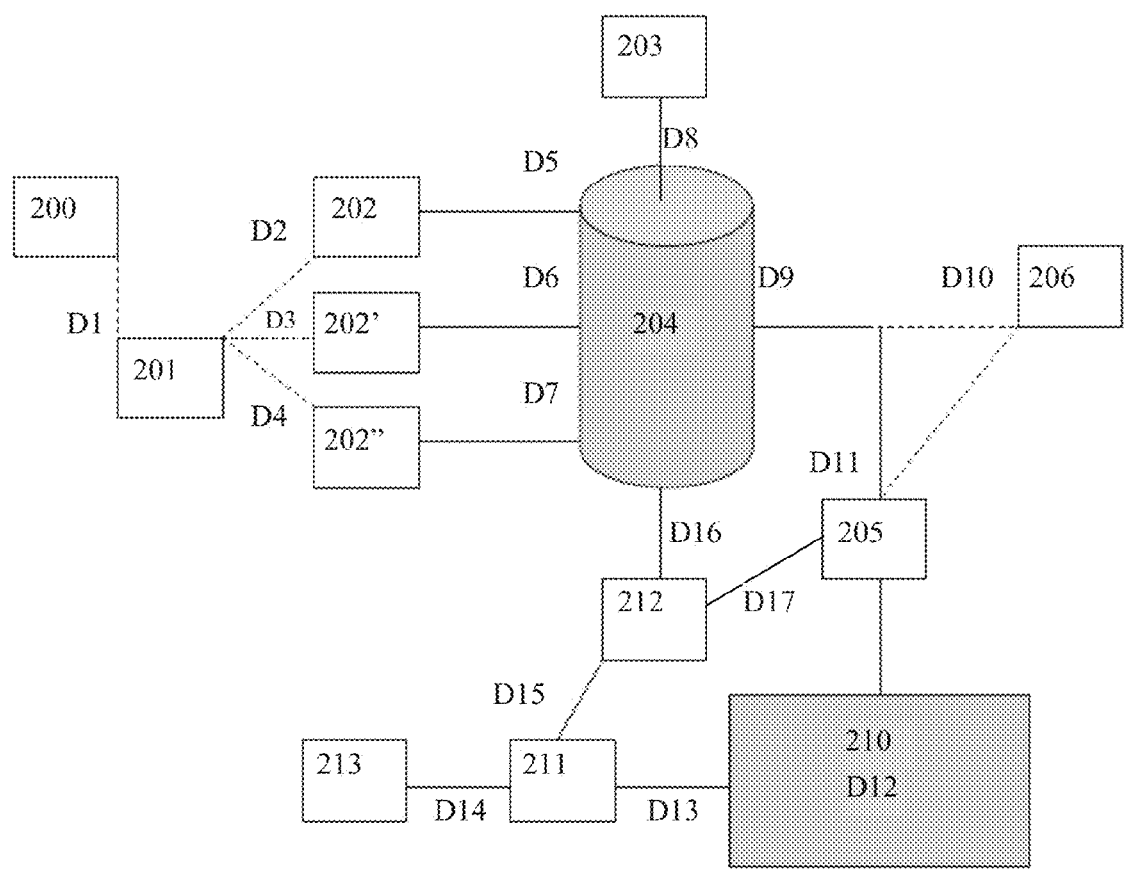
FIG. 2 shows a non-limiting global schematic illustrating where opticoanalytical devices (D) can be used in monitoring the process of forming a fluid, introducing a fluid into a subterranean formation, and producing a fluid from a subterranean formation.

FIG. 2 shows a non-limiting global schematic illustrating where opticoanalytical devices (D), according to some embodiments of the present invention, can be used in monitoring the process of forming a fluid, introducing a fluid into a subterranean formation, and producing a fluid from a subterranean formation. It is to be recognized that the placement of opticoanalytical devices (D) depicted in FIG. 2 should be considered illustrative in nature only for purposes of describing exemplary flow pathways used in forming and using fluids. As illustrated in FIG. 2, the recovery of a flow back fluid from a subterranean formation is also included and considered to be a part of the normal flow pathways for forming and using a fluid, according to the present embodiments. FIG. 2 depicts potential monitoring locations along an illustrative flow pathway used for forming a fluid, where opticoanalytical devices (D) can be used to monitor various characteristics of the fluid. The monitoring locations are optional, and potentially additive, based on the needs of a user. Depending on the user's needs, an opticoanalytical (D) device at one location can be used, or opticoanalytical devices (D) at multiple locations can be used in any combination that is suitable to the user. For example, in a particular implementation of a fluid formation, introduction and production process, it is anticipated that only some of the opticoanalytical devices (D) will be present, but this will be a matter of operational design for a user depending upon the level of monitoring and information needed by the user. Moreover, opticoanalytical devices (D) can be at locations other than those depicted in FIG. 2, and/or multiple opticoanalytical devices (D) can be placed at each depicted location or others. Without limitation, in some embodiments, the opticoanalytical devices (D) can be used in at least the following locations for monitoring a fluid being formed or introduced into/produced from a subterranean formation: at a supplier for a component of the fluid, on a transport means for the component, at a field site upon receipt of the component, at a storage site for the component, prior to and after combining one or more components to form a treatment fluid, during transport to and just before introduction into a subterranean formation, within a subterranean formation, and in the flow back fluid produced from the subterranean formation. Information that can be obtained at each of these locations, including process control resulting therefrom, will now be described in more detail.

Sourcing and Transport

Referring to FIG. 2, source material 200 can be monitored with an opticoanalytical device (D1) prior or during transfer of a material to transport means 201. In some embodiments, opticoanalytical device (D1) can be located at the exit of a container housing source material 200. In other embodiments, opticoanalytical device (D1) can be located in a tank or storage vessel housing source material 200. In still other embodiments, opticoanalytical device (D1) can be located on transport means 201.

Analyses that can be obtained at this stage include, without limitation, the identity, concentration and purity of source material 200. That is, opticoanalytical device (D1) can be used as an initial quality check to ensure that the proper source material has been obtained. The source material on transport means 201 can then be transported to storage areas 202, 202' and 202" at a job site. Although FIG. 2 has depicted a single transport means 2011 delivering the same source material to storage areas 202, 202' and 202", it is to be recognized that in most cases storage areas 202, 202' and 202" will each contain different materials that are transported by separate transport means 201. Further, it is to be recognized that any number of source materials can be utilized in the processes described herein. That is, the depiction of only three storage areas should not be considered limiting. Prior to depositing the source material in transport means 201 in any of storage areas 202, 202' or 202", opticoanalytical devices (D2-D4) can again be used to verify that the source material in transport means 201 has been delivered to the proper storage area and to verify that the source material has not degraded or otherwise changed during transport. It is to be further recognized that storage at a job site can optionally be omitted and the source material on transport means 201 can be directly combined with other materials to make a treatment fluid. Production of treatment fluids and monitoring thereof is discussed in greater detail hereinafter.

In the field of subterranean operations, source material 200 is most often obtained from a supplier at a location that is remote from a job site. Accordingly, transport means 201 is most typically a mobile carrier such as, for example, a truck, a railway car, boat or a barge. In FIG. 2, the lines connecting source material 200, transport means 201 and storage areas 202, 202' and 202" are broken to indicate that there is no fixed pathway therebetween. Although not typical in the field of subterranean operations, transport means 201 can alternately be a fixed pathway, such as a pipeline, for example, in alternative embodiments.

In addition, once the source material is in storage areas 202, 202' and/or 202", the source material can also be monitored with opticoanalytical devices (not shown) located within each storage area. The opticoanalytical devices within storage areas 202, 202' and/or 202" can be used, for example, to determine if the source material degrades or is otherwise changed during storage. Further, analysis of the source material while in storage areas 202, 202' and/or 202" can be utilized by an operator to determine the quantities of source material to be used in a treatment fluid for subterranean operations.

Combining Source Materials to Make a Treatment Fluid

After Obtaining one or more source materials at a job site, in some embodiments, combining of the source materials to make a treatment fluid can then take place. It is to be understood that the term "combining" does not imply any particular action for combining (e.g., mixing or homogenizing) or degree of combining unless otherwise noted. Referring again to FIG. 2, the source materials in storage areas 202, 202' and 202" can be combined with a base fluid in vessel 204 in order to form a treatment fluid therein. The source materials being transported from storage areas 202, 202' and 202" can again be monitored with opticoanalytical devices (D5-D7) prior to being introduced into vessel 204 to ensure that the proper source materials are present and that they have not degraded or otherwise changed during storage. Likewise, the characteristics of the base fluid from base fluid source 203 can be monitored using opticoanalytical device (D8). As discussed hereinafter, the base fluid can alternately be obtained from recycled fluid stream 212, as discussed in more detail hereinbelow. in either case, monitoring of the base fluid can be important to ensure that a treatment fluid having the desired characteristics is formed.

It is to be recognized that vessel 204 can take on many different forms, and the only requirement is that vessel 204 be suitable for combining the source material(s) with the base fluid. In some embodiments, vessel 204 be a mixer, blender or homogenizer. In some embodiments, vessel 204 can be a mixing tank. In some embodiments, vessel 204 can be a pipe. In still other embodiments, vessel 204 can utilize an air mixer to combine the source materials with a base fluid. In some embodiments, vessel 204 can be a reaction chamber in which at least some of the source materials react with one another upon forming the treatment In various embodiments, the base fluid can be an aqueous base fluid such as, for example, fresh water, acidified water, salt water, seawater, brine, aqueous salt solutions, surface water (i.e., streams, rivers, ponds and lakes), underground water from an aquifer, municipal water, municipal waste water, or produced water (e.g., from recycled fluid stream 212) from a subterranean formation, in alternative embodiments, the base fluid can be a non-aqueous base fluid such as, for example, a hydrocarbon base fluid. As will be evident to one having ordinary skill in the art, some treatment operations can be ineffective if the base fluid contains certain trace materials that prevent an effective treatment operation from occurring. For example, fracturing operations can be ineffective in the presence of certain ionic materials or some bacteria. Similarly, certain trace materials in a base fluid can interact in an undesired. fashion with a source material. For example, if the base fluid contains excess sulfate ions, a precipitate can form in the presence of barium ions from a source material. According to the present embodiments, a base fluid containing incompatibilities can be identified before the formation of a treatment fluid, thereby conserving valuable resources that could otherwise be wasted in producing an ineffective and potentially damaging treatment fluid.

It should again be noted that until vessel 204 is reached, the characteristics of the source material(s) and the base fluid are monitored prior to their being combined with one another. Thus, incorrect source materials or out of range characteristics can be readily identified and addressed according to the embodiments described herein. For example, the composition of the treatment fluid can be adjusted in order to address an out of range condition. As previously described, monitoring and control of the process can take place automatically in order to address out of range conditions as soon as possible.

Continuing now with FIG. 2, a treatment fluid formed in vessel 204 can be monitored after its formation to verify that it has the desired characteristics for performing a particular treatment operation. Monitoring can be performed using opticoanalytical device (D9) as the treatment fluid exits vessel 204. Alternately, opticoanalytical device (D9) can monitor the treatment fluid while in vessel 204. Thereafter, the treatment fluid can be transported to pump 205 for introduction into subterranean formation 2110. In the event that the treatment fluid has not been properly combined in vessel 204 or if its characteristics are not those desired, the treatment fluid can be diverted back into vessel 204 rather than being introduced into subterranean formation 210 (diversion pathway not shown). For example, a treatment fluid that was improperly mixed in vessel 204 might have an incorrect composition or have an out of range viscosity that can be remedied by continued mixing. Optionally, one or more additional source materials or the same source materials added previously can be added to address the out of range condition. Further optionally, the treatment fluid can be disposed of if its characteristics cannot be suitably altered by addition of one or more additional substances or by continued mixing. Although not optimal, the disposal of a treatment fluid presents less serious economic concerns than haphazardly introducing the treatment fluid downhole where it can potentially damage a subterranean formation.

In some embodiments, the treatment fluid can be formed in vessel 204 at a job site and directly transferred to pump 205 via a pipeline or other type of fixed transfer means. In some embodiments, the treatment fluid can be formed in vessel 204 at a remote site and transferred via mobile transfer means 206 where there is again not a fixed connection between vessel 204 and pump 205. The latter situation exists for offshore subterranean operations, wherein a treatment fluid can be formed onshore and transported via boat or barge to an offshore drilling platform for introduction downhole. As with transfer means 201, the treatment fluid can be monitored with opticoanalytical device (D10) as it is loaded on mobile transfer means 206 as a quality control check of the transfer process.

In the case of a treatment fluid formed at a job site, the monitoring of the treatment fluid prior to introduction into pump 205 is not typically of great concern, since the connection pathway thereto is usually fixed and the lag time between formation of the treatment fluid and downhole pumping is usually not lengthy. However, in the event that the treatment fluid is stored in vessel 204 or elsewhere prior to being introduced downhole, opticoanalytical device (D11) can be used to verify that the characteristics of the treatment fluid are still suitable for being introduced into the subterranean formation. Opticoanalytical device (D11) can be particularly useful for offshore subterranean operations. In the case of offshore subterranean operations, there can be a significant delay between the formation of a treatment fluid and downhole pumping, which can present the opportunity for degradation of the treatment fluid to occur. That is, a treatment fluid that was initially suitable, as measured by opticoanalytical device (D9), can change significantly in characteristics by the time it reaches an offshore site. In either case, the characteristics of the treatment fluid can again be monitored using opticoanalytical device (D11) as a final quality check before the treatment fluid is introduced. into subterranean formation 210. Further, the characteristics monitored using opticoanalytical device (D11) can be used, in some embodiments, as a baseline value to help evaluate the effectiveness of a treatment operation, as discussed in more detail hereinafter.

If the characteristics of the treatment fluid being introduced into subterranean formation 210 are not in the desired range, in some embodiments, the treatment operation can be stopped or the characteristics of the treatment fluid can be adjusted. In some embodiments, the treatment fluid can be returned to vessel 204 to adjust the characteristics of the treatment fluid. In other embodiments, the treatment operation can be continued, with one or more additional components being added at the well head while the treatment fluid is being introduced into the subterranean formation, referred to herein as "on-the-fly addition" (process not shown).

Monitoring a Treatment Operation and a Flow Back Fluid Produced from a Subterranean Formation Once introduced into subterranean formation 210, in some embodiments, one or more opticoanalytical devices (D12) can be used to monitor the treatment fluid while in the formation (e.g., in the well bore), Depending on the location(s) of the one or more opticoanalytical devices (D12) in subterranean formation 210 (e.g. in the well bore), various types of information on the treatment operation can be determined in real-time or near real-time based upon fluid flow into or out of subterranean formation 210. For example, in some embodiments, the consumption of a substance in the treatment fluid can be monitored as the treatment fluid passes through various subterranean zones. In other embodiments, the flow pathway of the treatment fluid in the subterranean formation can be monitored as it passes various opticoanalytical devices (D12). Information obtained from opticoanalytical devices (D12) can not only be used to map the morphology of the subterranean formation but also to indicate whether the characteristics of the treatment fluid need to be changed in order to perform a more effective treatment. For example, the treatment fluid can be modified in order to address specific conditions that are being encountered downhole. In addition, in some embodiments, the treatment fluid can be monitored to ensure that its characteristics do not change in an undesirable way when introduced into the downhole environment. In the event that the treatment fluid undesirably changes upon being introduced downhole, the treatment fluid being introduced into subterranean formation 210 can be modified, as described above, or an additional component can be introduced separately within subterranean formation 210 in order to address changes in characteristics that occur during transit downhole. In some embodiments, a treatment fluid can be monitored downhole using opticoanalytical devices (D12) in order to evaluate fluid displacement and fluid diversion in the subterranean formation (e.g, the flow pathway). In such embodiments, real-time or near-real time data from opticoanalytical devices (D12) can be used to adjust the placement of the fluid using diverting agents and to evaluate the effectiveness of diverting agents. In some embodiments, the diverting agents can be added to the treatment fluid in response to the characteristics Observed using opticoanalytical devices (D12). In other embodiments, fracture conductivity in the subterranean formation can be monitored using the opticoanalytical devices. In still other embodiments, a formation fluid can be monitored using opticoanalytical devices (D12).

In addition to monitoring a treatment operation while the treatment fluid is downhole, the flow back fluid produced from subterranean formation 210 can be monitored using opticoanalyticat device (D13) to provide information on the treatment operation. It is to be noted that monitoring the flow back fluid is where one would conventionally monitor the effectiveness of a treatment operation by collecting aliquots of the flow back fluid and conducting suitable laboratory analyses. In the present embodiments, the characteristics of the flow back fluid, as monitored using opticoanalytical device (D13), can be compared to the characteristics of treatment fluid being introduced into subterranean formation 210, as monitored using opticoanalytical device (D11). Any changes in characteristics, or lack thereof, can be indicative of the effectiveness of the treatment operation. For example, the total or partial consumption of a component in the flow back fluid (e.g., via chemical reactions in the subterranean formation) or the formation of a new substance in the flow back fluid can be indicative that at least some treatment effect has occurred. In some embodiments, a change in concentration of a component in the treatment fluid can be determined by monitoring the concentration in the flow back fluid using opticoanalytical device (D13) and the concentration of the component prior to its introduction into subterranean formation 210 using opticoanalytical device (D11) or another upstream opticoanalytical device. In some embodiments, the change in concentration can be correlated to an effectiveness of a treatment operation being performed in subterranean formation 210.

In some embodiments, the flow back fluid can comprise an aqueous base fluid that is produced from subterranean formation 210 as a result of a treatment operation. In other embodiments, the flow back fluid can comprise a formation water that is produced from subterranean formation 210, particularly as a result of a treatment operation. In still other embodiments, the flow back fluid can also comprise a produced hydrocarbon from subterranean formation 210.

After analysis, flow back fluid stream 211 can be directed in at least two different ways. In some embodiments, the flow back fluid can be analyzed and disposed of other embodiments, the flow back fluid can be analyzed and recycled.

In some embodiments, if an initial analysis of the flow back fluid is satisfactory using opticoanalytical device (D13), flow back fluid stream 211 can again be optionally analyzed with opticoanalytical device (D14) and sent to disposal stream 213, provided that the characteristics of the flow back fluid remain within acceptable disposal parameters. If the initial analysis of the flow back fluid is not satisfactory for disposal, as determined by opticoanalytical device (D13), flow back fluid stream 211 can have at least one additional substance added thereto in order to adjust its characteristics and make it suitable for disposal. For example, a flow back fluid that is too acidic can be at least partially neutralized and analyzed again using opticoanalytical device (D14) prior to disposal. Alternatively, flow back fluid stream 211 can have a substance removed therefrom in order to adjust its characteristics and make it suitable for disposal. For example, a metal contaminant in flow back fluid stream 211 can be removed by ion exchange techniques in an embodiment.

Preferably, flow back fluid stream 211 can be reused in subsequent subterranean operations such as, for example, as the base fluid of a treatment fluid (e.g., a fracturing fluid) or in a water flooding operation. In this regard, flow back fluid stream 211 can be monitored using opticoanalytical device (D15) and modified, if necessary, by adding at least one substance thereto or removing at least one substance therefrom, to produce recycled fluid stream 212. After forming recycled fluid stream 212, it can be monitored using opticoanalytical device (D16) to verify that it has the characteristics for forming another treatment fluid in vessel 204. The treatment fluid formed using recycled fluid stream 212 can be used in subterranean formation 210, in some embodiments, or transported to another subterranean formation in other embodiments. Alternately, recycled fluid stream 212 can be monitored using opticoanalytical device (D17) to ensure that it is suitable for being reintroduced into subterranean formation 210 or another subterranean formation. That is, in some embodiments, the flow back fluid produced from a first subterranean formation can be used in a water flooding operation in a second subterranean formation. It is to be noted that if no modification of flow back fluid stream 211 is needed, then formation of a treatment fluid or introduction into a subterranean formation can take place without further modification occurring.

In other embodiments, opticoanalytical device (D13) can be used to assay a non-aqueous fluid being produced from a subterranean formation. For example, opticoanalytical device (D13) can be used to determine the composition of a formation fluid (e.g., a hydrocarbon) being produced from the subterranean formation.

Monitoring the Formation and Transport of a Treatment Fluid

In various embodiments, the methods described herein can be used to monitor and control the formation and transport of any type of treatment fluid intended for introduction into a subterranean formation. Regardless of the intended form or function of the treatment fluid, any desired characteristic of the treatment fluid can be monitored according to some embodiments described herein. Without limitation, treatment fluids that can be monitored during their formation and transport according to the present embodiments can include, for example, fracturing fluids, gravel packing fluids, acidizing fluids, conformance control fluids, gelled fluids, fluids comprising a relative permeability modifier, diverting fluids, fluids comprising a breaker, biocidal treatment fluids, remediation fluids, and the like. Although several specific examples of treatment fluids are set forth hereinafter in which the present methods can be used for monitoring, it is to be recognized that these examples are illustrative in nature only, and other types of treatment fluids can be monitored by one having ordinary skill in the art by employing like techniques.

Illustrative substances that can be present in any of the treatment fluids of the present invention can include, for example, acids, acid-generating compounds, bases, base-generating compounds, surfactants, scale inhibitors, corrosion inhibitors, gelling agents, crosslinking agents, anti-sludging agents, foaming agents, defoaming agents, antifoam agents, emulsifying agents, de-emulsifying agents, iron control agents, proppants or other particulates, gravel, particulate diverters, salts, fluid loss control additives, gases, catalysts, clay control agents, chelating agents, corrosion inhibitors, dispersants, floccutants, scavengers (e.g., $H_2S$ scavengers, $CO_2$ scavengers or $O_2$ scavengers), lubricants, breakers, delayed release breakers, friction reducers, bridging agents, viscosifiers, weighting agents, solubilizers, rheology control agents, viscosity modifiers, pH control agents (e.g., buffers), hydrate inhibitors, relative permeability modifiers, diverting agents, consolidating agents, fibrous materials, bactericides, tracers, probes, nanoparticles, and the like. Combinations of these substances can be used as well.

In various embodiments, the treatment fluids used in practicing the present invention also comprise a base fluid. In some embodiments, the base fluid can be an aqueous base fluid. In other embodiments, the base fluid can be a non-aqueous base fluid, such as a hydrocarbon.

Figure 3:
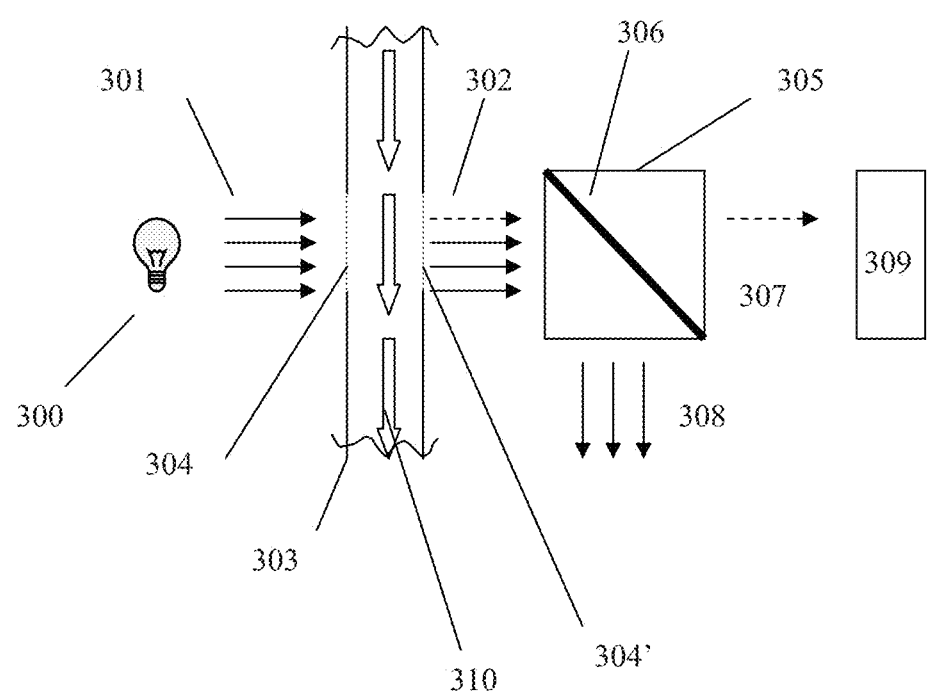
FIG. 3 shows an illustrative schematic demonstrating how an optical computing device can be implemented along a flow pathway used for transporting a fluid.

In various embodiments of the present invention, opticoanalytical devices (e.g., optical computing devices and ruggedized spectrometers) can be used to monitor a treatment fluid during its formation and transport. Monitoring of source materials to be used in the treatment fluid, including water, can also be performed by like techniques as a quality control measure. In some embodiments, monitoring of the treatment fluid and the source material can occur "in-line" or "in-process" along a flow pathway for transporting the treatment fluid or source material without the transport being interrupted or significantly altered. For example, the embodiment shown in FIG. 2 illustrates how an in-line process can be implemented in some embodiments, where the in-line monitoring can take place using at least one opticoanalytical device that is in optical communication with the flow pathway. As used herein, the term "in optical communication" refers to the condition of an opticoanalytical device being positioned along a flow pathway and the flow pathway being configured such that electromagnetic radiation reflected from, emitted by or transmitted through a fluid in the flow pathway is readable by the opticoanalytical device. FIG. 3, which is discussed in more detail hereinbelow, shows an embodiment in which an opticoanalytical device can be in optical communication with a flow pathway. In some embodiments, monitoring a fluid along a flow pathway (e.g., in a line) using an opticoanalytical device can take place white the fluid is flowing without the fluid transport. process being interrupted. In other embodiments, monitoring a fluid along a flow pathway can take place without the fluid being transported. That is, the fluid transport process can be temporarily interrupted while monitoring takes place, with the fluid remaining substantially static in the flow pathway during monitoring. in still other embodiments, the flow pathway can be configured to divert a portion of the fluid away from its main transport pathway, where monitoring of the fluid can take place using the diverted portion. In alternative embodiments, the fluid from the diverted portion can be removed from the system and analyzed using an opticoanalytical device at a job site, where the opticoanalytical device is not used in-process. That is, in such embodiments, the fluid can be monitored off-tine using a standalone opticoanalytical device.

Other than when the opticoanalytical device is located in the subterranean formation itself, the opticoanalytical device and the fluid that it is monitoring are not generally in direct physical contact with one another. Generally, the opticoanalytical device can be in optical communication with a fluid contained within a flow pathway, as described previously. However, in some alternative embodiments, the opticoanalytical device can be in direct physical contact with the fluid (e.g., in a tank or within a flow pathway). FIG. 3 shows an illustrative schematic demonstrating how an optical computing device can be implemented along a flow pathway used for transporting a fluid. As shown in FIG. 3, source 300 produces incident electromagnetic radiation 301, which interacts with fluid 310 within line 303 having window 304 defined therein. Window 304 is substantially transparent to incident electromagnetic radiation 301, allowing it to interact with fluid 310 therein. Interacted electromagnetic radiation 302 is changed by its interaction with fluid 310, and it exits though window 304', which is substantially transparent to interacted electromagnetic radiation 302, thereby allowing fluid 310 to be in optical communication with optical computing device 305. Some of interacted electromagnetic radiation 302 is related to a component of interest in the fluid, and the remaining interacted electromagnetic radiation 302 is due to interaction of the electromagnetic radiation with background materials or other components in the fluid. Interacted electromagnetic radiation 302 then enters optical computing device 305 having ICE 306 therein. ICE 306 then separates interacted electromagnetic radiation into components 307 and 308, related to the component of interest and other components, respectively. Electromagnetic radiation component 307 then interacts with detector 309 to provide information on the component of interest in fluid 310. Further details of the operation of the optical computing device were set forth previously hereinabove. In some embodiments, the output of detector 309 can be a voltage signal, which can be proportional to the concentration of the component of interest.

In some embodiments, methods for analyzing the formation and transport of a treatment fluid can comprise: providing at least one source material; combining the at least one source material with a base fluid to form a treatment fluid; and monitoring a characteristic of the treatment fluid using an opticoanalytical device. In some embodiments, the opticoanalytical device can be in optical communication with a flow pathway for transporting the treatment fluid (e.g., in-line monitoring). In other embodiments, monitoring a characteristic of the treatment. fluid can take place in an off-line manner.

Characteristics of the treatment fluid or source material that can be monitored can include both physical and chemical properties. Characteristics of a treatment fluid or a source material that can be monitored according to the present methods can include, without chemical composition identity, chemical composition concentration, chemical composition purity, viscosity, ionic strength, pH, total dissolved solids, total dissolved salt, density, and the like. In some embodiments, the characteristic of the treatment fluid can be determined directly from the output of a detector analyzing the electromagnetic radiation reflected from, emitted by or transmitted through the treatment fluid. For example, the identity and concentration of a component in a treatment fluid can be directly determined from a detector output (e.g., a voltage) based upon preestablished calibration curves. In other embodiments, the characteristic of the treatment fluid can be calculated based upon a concentration of one or more components in the treatment fluid, as determined using the opticoanalytical device. For example, a processing element can determine the viscosity, pH, sag potential, and/or any like physical property of the treatment fluid based upon the content of one or more components of the treatment fluid. Further, in some embodiments, the processing element can determine a characteristic of the treatment fluid based upon a linear combination of property contributions from each component of the treatment fluid.

In some embodiments, the processing element to determine a characteristic of the treatment fluid can be an artificial neural network, which can use training set information from treatment fluids having known properties and compositions in order to estimate the characteristics of treatment fluids having unknown content prior to analysis. By determining a linear combination of property contributions based upon each component of the treatment fluid, a more accurate estimation of an unknown treatment fluid's properties can be determined than if the analysis was based upon a single component. That is, the more completely an artificial neural network is trained using treatment fluids having known properties, the more likely it is to better estimate the characteristics of an unknown treatment fluid.

By employing the present methods, at least in some embodiments, a measure of quality control during the formation of a treatment fluid can be established. Conventionally, treatment fluids are not rigorously analyzed during their formation, or the analysis often can take place after the treatment fluid has already been introduced into a subterranean formation, at which point the analysis is only of use in a retrospective sense. The present methods overcome this limitation in the art and others by providing multiple opportunities to identify and adjust the characteristics of a treatment fluid before or during its introduction into a subterranean formation.

In some embodiments, a treatment fluid can be monitored immediately after combining a base fluid and at least one source material to form the treatment fluid. In some embodiments, monitoring can take place in a vessel in which the treatment fluid is formed. In some embodiments, monitoring can take place as the treatment fluid exits the vessel in which the treatment fluid is formed. In some embodiments, monitoring can take place as the treatment fluid is formed "on-the-fly." In some embodiments, the treatment fluid can be monitored at one or more points as it is transported from the vessel to be introduced into a subterranean formation.

In some embodiments, the present methods can further comprise transporting the treatment fluid to a pump after forming the treatment fluid. In some embodiments, the methods can further comprise introducing the treatment fluid into a subterranean formation, for example, by using the pump. In some embodiments, a characteristic of the treatment fluid can be monitored using an opticoanalytical device that is in optical communication with the fluid in a flow pathway to the subterranean formation. In such embodiments, the opticoanalytical device can be located at the pump or at a location near the pump, such that changes in the characteristics of the treatment fluid between its formation and subsequent introduction into a subterranean formation can be evaluated. The output from this opticoanalytical device can serve as the last line of defense to prevent a treatment fluid having an incorrect characteristic from being introduced into a subterranean formation. In some embodiments, transporting the treatment fluid to the pump can take place in a pipeline. In some embodiments, transporting the treatment fluid to the pump can take place via a mobile transport means such as a truck or railway car. In some embodiments, transporting the treatment fluid to the pump can take place by using a storage vessel on a boat or barge for transporting the treatment fluid to an offshore site.

In some embodiments, the present methods can further comprise determining if the characteristic of the treatment fluid being monitored makes the treatment fluid suitable for being introduced into a subterranean formation. In various embodiments, determining if the treatment fluid is suitable for being introduced into the subterranean formation can comprise determining if one or more components therein have an out of range concentration, determining if an unwanted component or other impurities are present, and/or determining if a physical characteristic of the treatment fluid is out of range, for example. Other criteria for determining the suitability of a treatment fluid to be introduced into a particular subterranean formation can be established by one having ordinary skill in the art. In some embodiments, determining if the characteristic makes the treatment fluid suitable for being introduced into the subterranean formation can take place automatically. For example, a computer or like processing element can be configured to determine if the value of a characteristic being monitored or estimated represents an out of range condition. In some embodiments, monitoring and determining the suitability of a treatment fluid for being introduced into a subterranean formation can take place via remote monitoring and control.

Upon determining that the treatment fluid is unsuitable, the present methods can optionally further comprise adjusting a characteristic of the treatment fluid. In some embodiments, upon determining that the treatment fluid is unsuitable for being introduced into the subterranean formation, adjustment of a characteristic of the treatment fluid can take place under operator control. For example, an operator can manually direct the addition of one or more components to the treatment fluid to adjust its composition and properties. The characteristic of the treatment fluid can thereafter be re-evaluated and the suitability for introduction into a subterranean formation determined. In some embodiments, the operator can manually add the one or more components to the treatment fluid. In other embodiments, the operator can regulate an amount of one or more components being added to the treatment fluid from one or more source streams. In some embodiments, adjustment of a characteristic of the treatment fluid can take place automatically under computer control. For example, as described above, if a characteristic of the treatment fluid is determined to be out of range, a computer or like processing element can direct that at least one component is added to the treatment fluid to correct the out of range condition. In some embodiments, an additional amount of a component already in the treatment fluid can be added to the treatment fluid until the characteristic being monitored is back in an acceptable range. In other embodiments, at least one additional component can be added to the treatment fluid in order to bring the characteristic being monitored back into range. For example, in the case of an acidizing fluid, if the acid concentration is determined to be too high, a quantity of a suitable base can be added to neutralize some of the acid, or additional base fluid can be added to the treatment fluid in order to lessen the concentration of the acid. In alternative embodiments, a component can be removed from the treatment fluid in order to adjust its characteristics. As described previously, the impact of adding additional components to a treatment fluid can impact other characteristics other than those being directly addressed, and when the adjustment takes place automatically under computer control, at least an estimation of the impact on these other characteristics can be determined. That is, when a characteristic of the treatment fluid is adjusted automatically, the computer or like processing element can evaluate if the chosen adjustment is expected to impact other characteristics of the treatment fluid in an undesired manner and compensate for the adjustment of other characteristics, if needed.

In some embodiments, an operator can adjust or reset a set point or a set range for a characteristic of a fluid that is being automatically controlled by computer. In some embodiments, an operator can direct the adjustment of a characteristic or change a set point for automatic control by computer at the location of the treatment operation or through a communication system from a remote location.

In some embodiments, combining the base fluid and at least one component of the treatment fluid can occur at the well head by "on-the-fly" addition of the at least one component. That is, the treatment fluid can be formed at the well head without being transported from another location in such embodiments. Alternately, a pre-made treatment fluid can be modified at the well head by on-the-fly addition of at least one additional component or adjusting the concentration of an existing component in some embodiments. Advantages of on-the-fly addition can include, for example, reduced volumes, lower transportation costs, minimization of excess materials at a job site, and less opportunity for degradation of the treatment fluid. Such on-the-fly addition does not allow the characteristics of the treatment fluid to be assayed according to conventional methodology before the treatment fluid is introduced into the subterranean formation. This represents a particular difficulty with regard to control over a treatment operation, since it can often be difficult to precisely determine how much of a component to add in order to produce a treatment fluid having a desired characteristic. The same can hold true even with treatment fluids that are pre-formulated before being transported to a job site. However, these difficulties in the art can be overcome through use of the methods of the present invention by using opticoanalytical devices for monitoring the treatment fluid during its formation and introduction into a subterranean formation.

In some embodiments, the present methods can further comprise monitoring a characteristic of at least one source material being used to form a treatment fluid by using an opticoanalytical device. In some embodiments, the opticoanalytical device can be in optical communication with a flow pathway for transporting the at least one source material. In some embodiments, the opticoanalytical device can be in a tank or other storage vessel housing the source material. In other embodiments, monitoring of the at least one source material can take place off-line. As discussed above, monitoring of the source material can serve as an additional quality check during the formation of a treatment fluid.

In some embodiments, methods of the present invention can comprise: preparing a treatment fluid; transporting the treatment fluid to a job site; introducing the treatment fluid into a subterranean formation at the job site; monitoring a characteristic of the treatment fluid at the job site using an opticoanalytical device; determining if the characteristic of the treatment fluid being monitored using the opticoanalytical device makes the treatment fluid suitable for being introduced into the subterranean formation; and optionally, if the treatment fluid is unsuitable, adjusting the characteristic of the treatment fluid. In some embodiments, the opticoanalytical device can be in optical communication with a flow pathway for transporting the treatment fluid. In other embodiments, monitoring using the opticoanalytical device can take place off-line.

In some embodiments, methods of the present invention can comprise: providing a treatment fluid that comprises a base fluid and at least one additional component; introducing the treatment fluid into a subterranean formation; and monitoring a characteristic of the treatment fluid using at least a first opticoanalytical device. In some embodiments, the opticoanalytical device can be in optical communication with a flow pathway for transporting the treatment fluid before the treatment fluid is introduced into the subterranean formation. In other embodiments, monitoring using the opticoanalytical device can take place off-line before the treatment fluid is introduced into the subterranean formation.

In some embodiments, methods of the present invention can comprise: forming a treatment fluid on-the-fly by adding at least one component to a base fluid stream; introducing the treatment fluid into a subterranean formation; and monitoring a characteristic of the treatment fluid while it is being introduced into the subterranean formation using an opticoanalytical device. In some embodiments, the methods can further comprise: determining if the characteristic of the treatment fluid being monitored using the opticoanalytical device makes the treatment fluid suitable for being introduced into the subterranean formation, and optionally, if the treatment fluid is unsuitable, adjusting the characteristic of the treatment fluid.

Monitoring Fluids in and Produced from a Subterranean Formation

In some embodiments, the present methods can further comprise introducing the treatment fluid into a subterranean formation. In some embodiments, the introduction into the subterranean formation can take place after determining that the treatment fluid is suitable for being introduced into the subterranean formation. In some embodiments, the treatment fluid can be modified while it is being introduced into the subterranean formation by adding at least one additional component thereto or adjusting the concentration of an existing component. In some embodiments, the treatment fluid can be modified while it is in a subterranean formation. According to the present embodiments, monitoring of a treatment fluid. in the subterranean formation or in a flow back fluid produced therefrom occurs in-process. Further, according to some of the present embodiments, a formation fluid can be monitored using an opticoanalytical device in the formation or in optical communication with a fluid being produced from the formation.

Additional information regarding the effectiveness of a treatment operation can be obtained by continued monitoring of the treatment fluid or a formation fluid while it is downhole or after the treatment fluid or formation fluid is produced from the subterranean formation. Monitoring of formation fluids (e.g. oil) while within the subterranean formation or after their production from the subterranean formation can also provide information on the effectiveness of a treatment operation and/or provide guidance on how a treatment operation can be modified in order to increase production. In some embodiments, the present methods can further comprise monitoring a characteristic of the treatment fluid and/or a formation fluid using an opticoanalytical device positioned in the formation. In other embodiments, the present methods can further comprise monitoring a characteristic of a fluid produced from a subterranean formation. The produced fluid can be a produced formation fluid in some embodiments or a treatment fluid produced as a flow back fluid in other embodiments. In some embodiments, the flow back fluid and/or the produced formation fluid can be monitored using an opticoanalytical device that is in optical communication with a flow pathway for transporting the flow back fluid. In some embodiments, the flow back fluid can comprise an at least partially spent treatment fluid from the performance of a subterranean treatment operation.

In some embodiments, the present methods can further comprise performing a treatment operation in the subterranean formation, and monitoring a characteristic of the treatment fluid and/or the formation fluid after the treatment fluid is introduced into the subterranean formation using an opticoanalytical device. In some embodiments, the treatment fluid and/or formation fluid can be monitored using an opticoanalytical device that is located in the subterranean formation. In some embodiments, the treatment fluid and/or formation fluid can be monitored using an opticoanalytical device that is in optical communication with a flow pathway for transporting a flow back fluid or formation fluid produced from the subterranean formation. In some embodiments, monitoring in the subterranean formation or of the flow back fluid and/or produced formation fluid can be conducted in-process during the performance of a treatment operation.

In some embodiments, the present methods can further comprise adjusting a characteristic of the treatment fluid being introduced into the subterranean formation in response to the characteristic of the treatment fluid or formation fluid being monitored using the opticoanalytical device in the formation or in optical communication with the flow back fluid pathway. For example, if the opticoanalytical device in the formation or monitoring the flow back fluid indicates that a component of the treatment fluid is spent, or that the treatment fluid no longer has a desired characteristic for adequately performing a treatment operation, the treatment fluid being introduced into the subterranean formation can be adjusted so as to modify at least one characteristic thereof, as described previously. Similarly, monitoring of the formation fluid can be used in models that evaluate the effectiveness of a treatment operation, for example. In some embodiments, adjustment of the characteristic of the treatment fluid in response to a characteristic measured in the formation or in the flow back fluid can take place automatically under computer control.

In some embodiments, methods described herein can comprise: providing a treatment fluid comprising a base fluid and at least one additional component; introducing the treatment fluid into a subterranean formation; allowing the treatment fluid to perform a treatment operation in the subterranean formation; and monitoring a characteristic of the treatment fluid or a formation fluid using at least a first opticoanalytical device. In some embodiments, the characteristic of the treatment fluid or the formation fluid can be monitored within the formation using the first opticoanalytical device. In some embodiments, the characteristic of the treatment fluid can be monitored in a flow back fluid produced from the formation, where the flow back fluid contains treatment fluid from the treatment operation. In some embodiments, the formation fluid can be monitored during production. In some embodiments, the characteristic of the treatment fluid and/or the formation fluid can both be monitored.

When monitoring a characteristic of the treatment fluid after introduction into a subterranean formation, monitoring the characteristic can comprise, in some embodiments, monitoring at least the identity and concentration of at least one component in the treatment fluid, the flow back fluid, or both. According to such embodiments, if one knows the concentration of the component prior to introduction into the subterranean formation, the change in concentration of the component while in the subterranean formation or after production from the subterranean formation (optionally in combination with information on the formation fluid) can provide information about the effectiveness of the treatment operation being conducted. For example, if the concentration of the component fails to change after being introduced into the subterranean formation, it can likely be inferred that the treatment operation had minimal to no effect on the subterranean formation. Likewise, if the concentration of the component decreases after being introduced into the subterranean formation, it is probable that the formation has been modified in some way by the treatment fluid. By monitoring the concentration of a component in a treatment fluid and/or formation fluid before and after introduction of the treatment fluid into a subterranean formation, a correlation between the effectiveness of a treatment operation can be established, in some embodiments. For example, the change in concentration of a component can be correlated to the effectiveness of a treatment operation being performed in the subterranean formation. Furthermore, if the treatment fluid becomes completely spent upon being introduced into the subterranean formation (that is, the concentration of at least one component therein drops below an effective level or even becomes zero), this can alert an operator or an automated system overseeing the treatment operation that the treatment fluid potentially needs to be altered or that the treatment operation potentially needs to be repeated, for example.

In order to determine a change in concentration of at least one component in a treatment fluid, the present methods can further comprise monitoring a characteristic of the treatment fluid before the treatment fluid is introduced into the subterranean formation. According to such embodiments, the (pre-introduction characteristic can serve as a baseline value for establishing whether a change in the characteristic has occurred upon being introduced into the subterranean formation. In some embodiments, the characteristic of the treatment fluid. before its introduction into the subterranean formation can be used as a basis for adjusting the characteristic of the treatment fluid being introduced into the subterranean formation.

In some embodiments, the present methods can further comprise determining if the characteristic of the treatment fluid being introduced into the subterranean formation needs to be adjusted in response to the characteristic of the treatment fluid or the formation fluid being monitored in the subterranean formation or in the flow back fluid using the opticoanalytical device. In some embodiments, the present methods can further include adjusting the characteristic of the treatment fluid being introduced into the subterranean formation in response to the characteristic of the treatment fluid or the formation fluid monitored. in the subterranean formation or in the flow back fluid. In some embodiments, adjusting the characteristic of the treatment fluid can take place automatically under computer control. In some embodiments, an artificial neural network can be used in the adjustment of the treatment fluid.

In some embodiments, tracers and/or probes can be deployed in the treatment fluids used in the present methods. As used herein, the term "tracer" refers to a substance that is used in a treatment fluid to assist in the monitoring of the treatment fluid in a subterranean formation or in a flow back fluid being produced from a subterranean formation. illustrative tracers can include, for example, fluorescent dyes, radionuclides, and like substances that can be detected in exceedingly small quantities. A tracer typically does not convey information regarding the environment to which it has been exposed, unlike a probe. As used herein, the term "probe" refers to a substance that is used in a treatment fluid to interrogate and deliver information regarding the environment to which it has been exposed. Upon monitoring the probe, physical and chemical information regarding a subterranean formation can be obtained.

In some embodiments, the present methods can further comprise monitoring a tracer or a probe in a treatment fluid using an opticoanalytical device. In some embodiments, the tracer or probe can be monitored in the flow back fluid produced from the subterranean formation. In other embodiments, the tracer or probe can be monitored within the subterranean formation. In the case of probes being monitored within a subterranean formation, the present methods can be particularly advantageous, since a probe that is produced in the flow back fluid can sometimes be altered such that it no longer conveys an accurate representation of the subterranean environment to which it has been exposed. In some embodiments, tracers or probes in the treatment fluid can be monitored using the opticoanalytical devices in order to determine a flow pathway for the treatment fluid in the subterranean formation. In some embodiments, monitoring of tracers or probes can be used to determine the influence of diverting agents on the flow pathway. Conventional methods for monitoring downhole fluid flow pathways can include, for example, distributed temperature sensing, as described in commonly owned United States Patent Application Publication 2011/0048708, which is incorporated herein by reference in its entirety.

In some embodiments, the treatment fluid being monitored by the present methods can be an aqueous treatment fluid. That is, the treatment fluids can comprise an aqueous base fluid. Suitable aqueous base fluids can include those set forth above. In some embodiments, a suitable aqueous base fluid can be produced water from a subterranean formation. The produced water can be formation water, in some embodiments, or the recovered aqueous base fluid from another aqueous treatment fluid in other embodiments. The aqueous base fluid can be monitored using an opticoanalytical device according to some of the present embodiments, as described elsewhere herein.

Monitoring of Produced Water and Reuse Thereof

Water treatment, conservation and management are becoming increasingly important in the oilfield industry. Oftentimes, significant water production can accompany hydrocarbon production in a well, whether from formation water or water used in a stimulation operation for the well. Increasingly strict environmental regulations have made disposal of this water a significant issue. Due to the volumes of water involved (millions of gallons per well), storage of this water while awaiting conventional analyses can be highly problematic. Water analyses conducted according to the embodiments described herein can address some of these limitations in the art and provide related advantages as well.

In some embodiments, the methods of the present invention can be applied toward monitoring a water obtained from a water source. In particular, in some embodiments, the water can comprise the base fluid being used to form a treatment fluid. In some embodiments, the water can be monitored to determine its suitability for disposal or for determining its characteristics in order to ascertain a remediation protocol to make it suitable for disposal. In some embodiments, methods of the present invention can comprise determining the suitability of a water for use as the base fluid of a treatment fluid and, if the water is not suitable for a particular treatment fluid, adjusting at least one characteristic of the water to make it suitable.

In some embodiments, the water being monitored by the methods of the present invention can be a produced water from a subterranean formation. The produced water can be formation water in some embodiments and/or comprise water from a base fluid that was part of a treatment fluid that performed a treatment operation in the subterranean formation (i.e., an aqueous flow back fluid) in other embodiments. As used herein, the term "produced water" refers to water obtained from a subterranean formation, regardless of its source. By determining the characteristics of the produced water, the suitability of the water for disposal or recycling as a base fluid in a subsequent treatment operation can be determined.

In some embodiments, methods described herein can comprise: providing water from a water source; monitoring a characteristic of the water using an opticoanalytical device; and introducing the water into a subterranean formation. In some embodiments, the opticoanalytical device can be in optical communication with a flow pathway for transporting the water.

In some embodiments, the water can be fresh water, acidified water, salt water, seawater, brine, aqueous salt solutions, saturated salt solutions, municipal water, municipal waste water, or produced water. The water source can be a surface water source such as, for example, a stream, a pond, an ocean, a detention pond, or a detention tank. In other embodiments, the water source can be a subterranean formation that provides the produced water. In some embodiments, a produced water can be formation water. In other embodiments, a produced water can be an aqueous flow back fluid obtained following a treatment operation. In some embodiments, the produced water can be a combination of formation water and an aqueous flow back fluid.

In some embodiments, the present methods can further comprise determining if the water is suitable for being introduced into the subterranean formation, and optionally, if the water is unsuitable, adjusting the characteristic of the water. As noted previously, determining the suitability of a fluid for introduction into a subterranean formation can be vital to the "health" of the subterranean formation, as the introduction of unwanted components can actually damage the subterranean formation or lead to an ineffective treatment operation. For example, the introduction of the wrong treatment fluid to a subterranean formation can lead to unwanted precipitation therein. Similarly, introduction of a treatment fluid containing bacteria can lead to biofouling or related damage that can impact production from a subterranean formation.

In some embodiments, the water can be introduced directly into the subterranean formation. For example, the water can be introduced into the subterranean formation as part of a water flooding operation. In some embodiments, the water can comprise a tracer or probe when being introduced into the subterranean formation. In some embodiments, the present methods can further comprise monitoring the tracer or probe in the subterranean formation using an opticoanalyticat device or in a flow back fluid produced from the subterranean formation.

In some embodiments, the water introduced into the subterranean formation can be used for environmental monitoring. That is, the water introduced into a subterranean formation can be monitored at well sites remote from the injection point to ascertain the movement of a fluid through and out of a subterranean formation. In some embodiments, an opticoanalytical device of the present invention can be used for monitoring the water at the remote well sites. In some embodiments, tracers or probes can be used in the water when environmental monitoring applications are conducted.

In other embodiments, the water can be introduced into the subterranean formation in a treatment fluid. That is, in some embodiments, the treatment fluid can comprise the water. In some embodiments, a property of the water can be adjusted by adding at least one additional component to the water. In some embodiments, the combination of the water and the at least one other component can be considered to constitute the treatment fluid. In other embodiments, a property of the water can be adjusted by adding at least one other component to the water prior to forming the treatment fluid, and still another additional component can be added thereafter to form the treatment fluid. That is, a treatment fluid formed in such a manner comprises at least two additional components. A reason one might form a treatment fluid in this manner is if a characteristic of the unmodified water would be detrimental to a component being used to form the treatment fluid. In this case, a first component could be added to adjust the characteristic of the water so as to no longer be detrimental to the second component being added subsequently. In alternative embodiments, a property of the water can be adjusted by removing at least one component from the water prior to forming a treatment fluid or by performing at least one water treatment on the water.

In some embodiments, methods of the present invention can further comprise combining at least one additional component with the water so as to alter at least one property thereof In some embodiments, the methods can further comprise monitoring a characteristic of the water using an opticoanalytical device after adding the at least one additional component. In some embodiments, monitoring the characteristic of the water after adding the at least one additional component can take place using an opticoanalytical device that is in optical communication with a flow pathway for transporting the water. In such embodiments, the opticoanalytical device can be used to ascertain if the at least one additional component has altered the characteristic of the water in desired fashion. For example, after adding the at least one additional component, the opticoanalytical device can be used to determine if a component added to the water (which can be a component already in the water) lies within a desired concentration range. In alternative embodiments, monitoring of the water using the opticoanalytical device can take place offline. In some embodiments, combining the at least one additional component with the water can take place automatically under computer control in response to a characteristic of the water monitored using an opticoanalytical device. In some embodiments, remote monitoring and adjustment can be conducted.

In some embodiments, methods of the present invention can comprise: producing water from a first subterranean formation, thereby forming a produced water; monitoring a characteristic of the produced water using an opticoanalytical device; forming a treatment fluid comprising the produced water and at least one additional component; and introducing the treatment fluid into the first subterranean formation or a second subterranean formation. In some embodiments, the opticoanalytical device can be in optical communication with a flow pathway for transporting the produced water. In other embodiments, monitoring the characteristic of the water using the opticoanalytical device can take place off-line, In some embodiments, the methods can further comprise monitoring a characteristic of the treatment fluid using another opticoanalytical device. In some embodiments, the opticoanalytical device used for monitoring the treatment fluid can be in optical communication with a flow pathway for transporting the treatment fluid. In other embodiments, monitoring of the treatment fluid using the opticoanalytical device can take place off-line. In some embodiments, the treatment fluid can be monitored using the opticoanalytical device before it has been introduced into the subterranean formation. In other embodiments, the treatment fluid can be monitored after it has been introduced into the subterranean formation, either in the formation itself or in a flow back fluid produced from the subterranean formation. In some embodiments, the formation fluid can also be monitored.

In some embodiments, methods of the present invention can comprise: providing water from a water source; monitoring a characteristic of the water using an opticoanalytical device; and treating the water so as to alter at least one property thereof. In some embodiments, treating the water can be conducted in response to the characteristic of the water monitored using the opticoanalytical device. In some embodiments, the opticoanalytical device can be in optical communication with a flow pathway for transporting the water.

In some embodiments, treating the water can comprise adding at least one component to the water. In some embodiments, treating the water can comprise increasing the concentration of an existing component in the water. In other embodiments, treating the water can comprise removing at least one component from the water. For example, the water can be subjected to a water purification technique. Illustrative water purification techniques are well known in the art and can include, for example, filtration, treatment with activated carbon, ion-exchange, reverse osmosis and the like. Generally, these water purification techniques remove at least one component from the water or modify at least one component in the water in order to modify the water's properties. In some embodiments, the water can be monitored with an opticoanalytical device after the water treatment takes place in order to determine if the water has the characteristics desired. In some embodiments, treating the water can comprise a bactericidal treatment such as, for example, exposure to ultraviolet light, electrocoagulation, or ozonolysis.

In some embodiments, the water can be selectively treated to remove, inactivate, or destroy components that can interfere with the formation of a treatment fluid or the effectiveness of a treatment fluid in a subterranean formation. For example, a water treatment process can be designed to render the water suitable for use in a treatment fluid without complete purification being achieved. Suitable water treatment processes for oilfield treatment fluids are described in commonly owned U.S. patent applications Ser. Nos. 12/722,410; 13/007,363; and 13/007,369, now available, respectively, as U.S. Patent Application Publications 2011/0220371, 2012/0181028, and 2012/0181014, each of which is incorporated herein by reference in its entirety.

In some embodiments, the present methods can further comprise disposing of the water after treating the water. In such embodiments, the water treatment can be chosen so as to make the water suitable for disposal. In some embodiments, the water can be monitored using an opticoanalytical device after being treated so as to verify that the water has been modified in a desired way, thereby making it suitable for disposal. In alternative embodiments, the water can be disposed of without additional treatment taking place if it is determined, using an opticoanalytical device, that the water is already suitable for disposal.

In some embodiments, water being produced from a subterranean formation can be recycled for use as the base fluid of a treatment fluid being introduced into the same subterranean formation or a different subterranean formation. Various types of treatment fluids that can be produced and monitored according to the methods described herein have been set forth previously. Depending on the intended treatment operation, the characteristic(s) of the water being monitored will likely vary from application to application. For example, when performing a fracturing operation, the certain ionic species, if present, can impact the outcome of a fracturing operation. Likewise, in an acidizing operation, particularly of a silica-containing subterranean formation, the presence of calcium ions in the base fluid can cause unwanted precipitation during the acidizing operation. In some cases, the water can contain materials that, if present, can lead to ineffective crosslinking of crosslinking agents and therefore impact the treatment fluid's rheological profile.

In some embodiments, treatment fluids comprising water, particularly water produced from a subterranean formation, can be used as fracturing fluids. In such embodiments, the treatment fluid can be introduced into a subterranean formation at a pressure sufficient to create or enhance at least one fracture therein. In some embodiments, monitoring a characteristic of a water to be used in a treatment operation can comprise monitoring the water for an ionic material. In this regard, the present methods can be particularly advantageous, since certain ionic materials, if present, can detrimentally impact a fracturing operation. These ionic materials can include, for example, iron-containing ions (e.g., $Fe^{2+}$, $Fe^{3+}$ and iron containing complex ions), iodine-containing ions (e.g., $I^-$ and $I_3^-$), boron-containing ions (e.g., $BO_3^-$), sulfur-containing ions (e.g., $SO_4^{2-}$, $SO_3^{2-}$ and $S^{2-}$), barium ions, strontium ions, magnesium ions, or any combination thereof. Other components of the water can also be detrimental to fracturing operations and will be recognized by one having ordinary skill in the art. For example, other ionic materials that can be of interest to monitor in a water can include, for example, carbonate ions, sodium ions, potassium ions, aluminum ions, calcium ions, manganese ions, lithium ions, cesium ions, chromium ions, fluoride ions, chloride ions, bromide ions, iodide ions, arsenic ions, lead ions, mercury ions, nickel ions, copper ions, zinc ions, titanium ions and the like. In addition, the presence of certain dissolved minerals in the water can also be of interest. Neutral molecules such as, for example, molecular iodine and boric acid can also be problematic as well. Still further, dissolved organic compounds in the water can also be monitored by using opticoanalytical devices according to the present methods.

Without being bound by any theory or mechanism in the following discussion, it is believed that certain ionic materials can be detrimental to fracturing operations for a number of different reasons. For example, sodium and potassium ions can affect hydration of polymers. Other ions such as, for example, borate, iron, sodium and aluminum ions can compete for crosslinking sites. In addition, some characteristics of a water can affect the ability to control the pH of a fluid produced therefrom. All of these factors can influence the overall rheological properties and ultimate performance of a fracturing fluid.

In some embodiments, detection of the ionic materials can take place directly using the opticoanalytical device. In some embodiments, the opticoanalytical device can be specifically configured to detect the ionic materials of interest. In other embodiments, dyes or other molecular tags can be used that react with the ionic materials in order to produce a detectable species. That is, the opticoanalytical device can be specifically configured to detect the reaction product of the dye or tag with the ionic species. Dyes and tags can be used, for example, when the ionic species is not readily detectable alone or if the sensitivity is not as great as desired. Other types of components in the water can be detected using dyes and tags as well.

It should be noted that the monitoring of water obtained from a water source is not limited to ionic materials. For example, in some embodiments, neutral substances (e.g., boric acid, molecular iodine, and organic compounds) can be monitored. In other embodiments, biologics such as bacteria and the like can be monitored using the present methods.

In some embodiments, upon identification of a substance in the water that is known to be detrimental to fracturing operations or another type of treatment operation, a characteristic of the water can be adjusted by adding at least one additional component thereto. In some embodiments, the addition of the at least one additional component to the water can create a treatment fluid having a custom formulation that is not typically used when a water source having a relatively consistent composition is used for forming a treatment fluid. Specifically, a water from a surface water source can many times have a composition that is relatively consistent from batch to batch, unless a contamination event has occurred, allowing treatment fluids having known, relatively constant compositions to be formulated. In contrast, a produced water can have a widely varying composition from batch to batch, depending on the type of subterranean formation from which it was obtained and any treatment operation that was previously performed in the subterranean formation. In order to address the variable characteristics of produced water, an array of additional components can be added thereto, some of which may not be commonly used in treatment fluids. In this regard, methods of the present invention can be particularly advantageous, as they can be capable of addressing the widely varying compositions encountered in produced waters by making predictive estimations of properties and conducting automatic adjustment and monitoring of those properties under computer control during the addition of at least one component to the produced water.

Applications to Fracturing Fluids and Fracturing Operations

In some embodiments, methods of the present invention can be used to monitor the formation of fracturing fluids and the performance of fracturing fluids during fracturing operations conducted in a subterranean formation. In addition to the issues with fracturing fluids noted above, other fracturing components in the fracturing fluid can be monitored using the present methods to determine the suitability of a fracturing fluid for performing a fracturing operation and to evaluate the effectiveness of a fracturing operation. Particularly, the present methods can be used to monitor a characteristic of a fracturing fluid during its formation and subsequent introduction into a subterranean formation at a pressure sufficient to create or enhance at least one fracture therein.

As non-limiting examples of how the present methods can be advantageous for monitoring a fracturing fluid, the present methods can be used to monitor a fracturing fluid's viscosity or the type of proppant particulates therein. A fracturing fluid having an insufficient viscosity may not have the capacity for supporting a proppant in the fracturing fluid, thereby leading to the failure of a fracturing operation. Likewise, the wrong type, size or concentration of proppant particulates can lead to the failure of a fracturing operation. Similar characteristics can be monitored during a fracturing operation in order to evaluate its effectiveness.

According to the present embodiments, the fracturing fluid can comprise any number of fracturing fluid components. In at least some embodiments, the fracturing fluid can contain at least a base fluid and proppant particulates, in addition to other fracturing fluid components. Other fracturing fluid components that can be present in the fracturing fluid include, for example, a surfactant, a gelling agent, a crosslinking agent, a crosslinked gelling agent, a diverting agent, a salt, a scale inhibitor, a corrosion inhibitor, a chelating agent, a polymer, an anti-sludging agent, a foaming agent, a buffer, a clay control agent, a consolidating agent, a breaker, a fluid loss control additive, a relative permeability modifier, a tracer, a probe, nanoparticles, a weighting agent, a rheology control agent, a viscosity modifier (e.g., fibers and the like), and any combination thereof. Any of these fracturing fluid components can influence the characteristics of the fracturing fluid and can be monitored according to the methods described herein using opticoanalytical devices.

In some embodiments, methods for forming a fracturing fluid can comprise: providing at least one fracturing fluid component; combining the at least one fracturing fluid component with a base fluid to form a fracturing fluid; and monitoring a characteristic of the fracturing fluid using an opticoanalytical device. In some embodiments, the opticoanalytical device can be in optical communication with a flow pathway for transporting the fracturing fluid.

In some embodiments, monitoring a characteristic of the fracturing fluid can comprise monitoring at least the identify and concentration of the at least one fracturing fluid. component in the fracturing fluid by using the opticoanalytical device. For example, in some embodiments, the identity and concentration of proppant particulates or a surfactant can be monitored in the fracturing fluid. In some embodiments, monitoring a characteristic of the fracturing fluid can comprise monitoring the fracturing fluid for impurities using the opticoanalytical device. In some embodiments, the impurities can be known impurities, where the opticoanalytical device has been configured to detect those impurities. In other embodiments, the impurities can be unknown impurities, where the presence of the impurities can be inferred by the characteristics of the fracturing fluid determined by the opticoanalytical device.

In some embodiments, the present methods can further comprise transporting the fracturing fluid to a pump, and introducing the fracturing fluid into a subterranean formation at a pressure sufficient to create or enhance at least one fracture therein. In some embodiments, a characteristic of the fracturing fluid can be monitored while being transported to the pump by using an opticoanalytical device located at the pump.

In some embodiments, the present methods can further comprise determining if the characteristic of the fracturing fluid being monitored makes the fracturing fluid suitable for being introduced into the subterranean formation, and optionally, if the fracturing fluid is unsuitable, adjusting the characteristic of the fracturing fluid. In some embodiments, determining if the fracturing fluid is suitable and adjusting the characteristic of the fracturing fluid can take place automatically under computer control. In some embodiments, adjusting the characteristic of the fracturing fluid can take place manually. In some embodiments, adjusting the characteristic of the fracturing fluid can comprise adjusting the concentration of at least one fracturing fluid component in the fracturing fluid or adding at least one additional fracturing fluid component to the fracturing fluid.

In some embodiments, monitoring the characteristic of the fracturing fluid and adjusting the characteristic of the fracturing fluid can take place by remote monitoring. Automated control and remote operation can be particularly advantageous for fracturing operations. Information from the opticoanalytical devices can be integrated with fracturing equipment information in real-time or near real-time to monitor and control fracturing operations. In addition, the fracturing information, including information from opticoanalytical devices, can be sent by satellite, wide area network systems or other communication systems to a remote location to further enhance job execution. Monitoring and control of the fracturing operation can then take place from this remote location. In some embodiments, remote operation can take place automatically under computer control.

In some embodiments, the present methods can further comprise introducing the fracturing fluid into a subterranean formation at a pressure sufficient to create or enhance at least one fracture therein. In some embodiments, the methods can further comprise monitoring a characteristic of the fracturing fluid or a formation fluid using an opticoanalytical device within the subterranean formation. In some embodiments, the present methods can further comprise producing a flow back fluid from the subterranean formation and monitoring a characteristic of the flow back fluid or a produced formation fluid using an opticoanalytical device. In some embodiments, the opticoanalytical device monitoring the flow back fluid or produced formation fluid can be in optical connection with a flow pathway for transporting the flow back fluid.

In some embodiments, methods described herein can comprise: providing a fracturing fluid comprising at least one fracturing fluid component; introducing the fracturing fluid into a subterranean formation at a pressure sufficient to create or enhance at least one fracture therein; and monitoring a characteristic of the fracturing fluid using an opticoanalytical device. In some embodiments, the opticoanalytical device can be in optical communication with a flow pathway for transporting the fracturing fluid before introducing the fracturing fluid into the subterranean formation.

In some embodiments, the methods can further comprise performing a fracturing operation in the subterranean formation and monitoring a characteristic of the fracturing fluid or a formation fluid after the fracturing fluid is introduced into the subterranean formation using another opticoanalytical device. In such embodiments, the opticoanalytical device can be located in the subterranean formation or in optical communication with a flow pathway for transporting a flow back fluid produced from the subterranean formation. In some embodiments, the characteristic of the fracturing fluid being introduced into the subterranean formation can be adjusted in response to the characteristic of the fracturing fluid or the formation fluid being monitored using the opticoanalytical device in the subterranean formation or monitoring the flow back fluid or produced formation fluid.

In some embodiments, methods for monitoring a fracturing fluid can comprise: forming a fracturing fluid on-the-fly by adding at least one fracturing fluid component to a base fluid stream; introducing the fracturing fluid into a subterranean formation at a pressure sufficient to create or enhance at least one fracture therein; and monitoring a characteristic of the fracturing fluid while it is being introduced into the subterranean formation using an opticoanalytical device. In some embodiments, the methods can further comprise determining if the characteristic of the fracturing fluid being monitored using the opticoanalytical device makes the fracturing fluid suitable for being introduced into the subterranean formation, and, optionally, if the fracturing fluid is unsuitable, adjusting the characteristic of the fracturing fluid.

In some embodiments, methods described herein can comprise: providing a fracturing fluid comprising a base fluid and at least one fracturing fluid component; introducing the fracturing fluid into a subterranean formation at a pressure sufficient to create or enhance at least one fracture therein, thereby performing a fracturing operation in the subterranean formation; and monitoring a characteristic of the fracturing fluid or a formation fluid using an opticoanalytical device. In some embodiments, the characteristic of the fracturing fluid or the formation fluid can be monitored in-process within the subterranean formation, in a flow back fluid or formation fluid produced from the subterranean formation, or both, while the fracturing operation is being conducted.

In some embodiments, the methods can further comprise determining if the characteristic of the fracturing fluid being introduced into the subterranean formation needs to be adjusted in response to a concentration of at least one fracturing component being monitored with an opticoanalytical device in the subterranean formation, or in optical communication with a flow pathway of a flow back fluid being produced from the subterranean formation. In some embodiments, the methods can further comprise adjusting the characteristic of the fracturing fluid being introduced into the subterranean formation. In some embodiments, determining if the characteristic of the fracturing fluid needs to be adjusted and adjusting the characteristic of the fracturing fluid can take place automatically under computer control.

In some embodiments, methods for performing a fracturing operation can further comprise monitoring a characteristic of the fracturing fluid using an opticoanalytical device that is in optical communication with a flow pathway for transporting the fracturing fluid, where monitoring takes place before the fracturing fluid is introduced into the subterranean formation. In some embodiments, the methods can comprise determining a change in concentration of at least one fracturing fluid component, based upon monitoring of the component before and after the fracturing fluid is introduced into the subterranean formation. In some embodiments, the change in concentration of the at least one fracturing fluid component can be correlated to an effectiveness of the fracturing operation being conducted in the subterranean formation. In some embodiments, the concentration of a component in a formation fluid can likewise be correlated to an effectiveness of the fracturing operation as well.

Analyses of produced fluids resulting from a fracturing operation (i.e., flow back fluids and formation fluids) can be used in models to estimate reservoir and fracture properties. The methods described herein can be used to supplement and beneficially increase the speed of these analyses, in particular, the composition of flowback water and formation water can be modeled to obtain information on permeability, conductivity, fracture dimensional features, and related information (See Gdanski et al, "A New Model for .Matching Fracturing Fluid Flowback Composition," SPE 106040 presented at the 2007 SPE Hydraulic Fracturing Technology Conference held in College Station, Tex., U.S.A., Jan. 29-31, 2007 and Gdanski et al, "Using Lines-of-Solutions to Understand Fracture Conductivity and Fracture Cleanup," SPE 142096 presented at the SPE Production and Operations Symposium held in Oklahoma City, Okla., U.S.A., Mar. 27-29, 2011). Methods for estimating properties of a subterranean formation and determining fracture characteristics in a subterranean formation from flowback fluid data are also described in commonly owned U.S. Pat. No. 7,472,748, which is incorporated herein by reference in its entirety.

In some embodiments, a tracer or probe in the fracturing fluid can be monitored using an opticoanalytical device. Monitoring the tracer or probe can also be beneficial for determining the effectiveness of a fracturing operation. For example, by monitoring a tracer or probe in the fracturing fluid using an opticoanalytical device, a flow pathway within the subterranean formation can be determined, in some embodiments.

In some embodiments, the present methods can be used to monitor a flow pathway of a fracturing fluid to which has been added a diverting agent. For example, one or more opticoanalytical devices in a subterranean formation can be used to determine where a fracturing fluid or other treatment fluid is flowing before the diverting agent is added to the treatment fluid. After the diverting agent is added, the opticoanalytical devices can be used to determine if the flow pathway has changed within the subterranean formation.

In some embodiments, methods described herein can comprise: providing a fracturing fluid comprising a base fluid and at least one fracturing fluid component; introducing the fracturing fluid into a subterranean formation at a pressure sufficient to create or enhance at least one fracture therein; and monitoring a characteristic of the fracturing fluid using an opticoanalytical device before the fracturing fluid is introduced into the subterranean formation. In some embodiments, the opticoanalytical device can be in optical communication with a flow pathway for transporting the fracturing fluid. In some embodiments, the methods can further comprise monitoring a characteristic of the fracturing fluid or a formation fluid after the fracturing fluid is introduced into the subterranean formation, where the fracturing fluid can be monitored in-process within the subterranean formation or in a flow back fluid produced from the subterranean formation.

In some embodiments, the present methods can further comprise monitoring at least the identity and concentration of at least one fracturing fluid component using an opticoanalytical device, before the fracturing fluid component is used to form a treatment fluid. In some embodiments, monitoring the at least one fracturing fluid component can be conducted with an opticoanalytical device that is in optical communication with a flow pathway for transporting the fracturing fluid component. In other embodiments, the opticoanalytical device can be located in a storage vessel for the fracturing fluid component.

Applications to Acidizing Fluids and Acidizing Operations

In some embodiments, methods of the present invention can be used to monitor the formation of acidizing fluids and the performance of acidizing operations in a subterranean formation. In various embodiments, the acidizing fluids can contain at least one acid. Most typically, the at least one acid can be selected from hydrochloric acid, hydrofluoric acid, formic acid, acetic acid, glycolic acid, lactic acid, and the like. Hydrochloric acid is typically used for acidizing limestone and carbonate-containing subterranean formations. Hydrofluoric acid is typically used for acidizing silicate-containing formations, including sandstone. It should be recognized by one having ordinary skill in the art that other acids or mixtures of acids can be used as well. The choice of an acid blend suitable for a particular subterranean formation will most often be a matter of routine design for one having ordinary skill in the art. In addition, suitable compounds that form acids downhole (i.e., acid precursors) can also be used. For example, esters, orthoesters and degradable polymers such as polylactic acid can be used to generate an acid in the subterranean formation. As one of ordinary skill in the art will also appreciate, the introduction of an acidizing fluid not having the proper characteristics or composition during an acidizing operation can have significant consequences on the success thereof, as damage to the subterranean formation can occur if the wrong acid is used. For example, precipitation of formation solids can occur in certain instances.

In addition to at least one acid, acidizing fluids suitable for use in the present embodiments can also contain other components in addition to the at least one acid. Two of the more notable components are chelating agents and/or corrosion inhibitors, for example. Chelating agents can slow or prevent the precipitation of formation solids, even when the proper acid is used during the treatment operation. Corrosion inhibitors can slow or prevent the degradation of metal tools used during the performance of an acidizing operation. If either of these components are out of range in an acidizing fluid being introduced into a subterranean formation, serious consequences in the performance of an acidizing operation can result. Other components that can optionally be present in the acidizing fluid include for example, a surfactant, a gelling agent, a salt, a scale inhibitor, a polymer, an anti-sludging agent, a diverting agent, a foaming agent, a buffer, a clay control agent, a consolidating agent, a breaker, a fluid loss control additive, a relative permeability modifier, a tracer, a probe, nanoparticles, a weighting agent, a rheology control agent, a viscosity modifier, and any combination thereof. Any of these additional components can also be monitored using an opticoanalytical device according to the methods described herein.

In some embodiments, methods for forming an acidizing fluid can comprise: providing at least one acid; combining the at least one acid with a base fluid to form an acidizing fluid; and monitoring a characteristic of the acidizing fluid using an opticoanalytical device. In some embodiments, the opticoanalytical device can be in optical communication with a flow pathway for transporting the acidizing fluid.

In some embodiments, monitoring a characteristic of the acidizing fluid can comprise monitoring at least the identity and concentration of the at least one acid in the acidizing fluid by using the opticoanalytical device. In some embodiments, monitoring a characteristic of the acidizing fluid can comprise monitoring at least the identity and concentration of at least one additional component in the acidizing fluid using the opticoanalytical device. Additional components can include those set forth above. In some embodiments, monitoring a characteristic of the acidizing fluid can comprise monitoring the acidizing fluid for impurities using the opticoanalytical device. In some embodiments, the impurities can be known impurities, where the opticoanalytical device has been configured to detect those impurities. In other embodiments, the impurities can be unknown impurities, where the presence of the impurities can be inferred by the characteristics of the acidizing fluid determined by the opticoanalytical device.

In some embodiments, the present methods can further comprise transporting the acidizing fluid to a pump, and introducing the acidizing fluid into a subterranean formation. In some embodiments, a characteristic of the acidizing fluid can be monitored using an opticoanalytical device white being transported to the pump. In some embodiments, the opticoanalytical device can be located at the pump.

In some embodiments, the present methods can further comprise determining if the characteristic of the acidizing fluid being monitored makes the acidizing fluid suitable for being introduced into the subterranean formation, and optionally, if the acidizing fluid is unsuitable, adjusting the characteristic of the acidizing fluid. In some embodiments, adjusting the characteristic of the acidizing fluid can take place automatically under computer control. In some embodiments, adjusting the characteristic of the acidizing fluid can take place manually. In some embodiments, adjusting the characteristic of the acidizing fluid can comprise adjusting the concentration of the at least one acid therein. In some embodiments, adjusting the characteristic of the acidizing fluid can take place through remote monitoring and control.

In some embodiments, the present methods can further comprise introducing the acidizing fluid into a subterranean formation. In some embodiments, the methods can further comprise monitoring a characteristic of the acidizing fluid or a formation fluid using an opticoanalytical device within the subterranean formation. In some embodiments, the present methods can further comprise producing a flow back fluid from the subterranean formation and monitoring a characteristic of the flow back fluid or a produced formation fluid using an opticoanalytical device that is in optical communication with a flow pathway for transporting the flow back fluid. In some embodiments, monitoring a characteristic of the acidizing fluid in the subterranean formation or in the flow back fluid produced from the subterranean formation can occur in-process while an acidizing operation is being performed.

In some embodiments, the present methods can further comprise adjusting a characteristic of the acidizing fluid being introduced into the subterranean formation in response to a characteristic of the acidizing fluid being monitored using an opticoanalytical device located at a pump for introducing the acidizing fluid into the subterranean formation.

In some embodiments, methods described herein can comprise: providing an acidizing fluid comprising at least one acid; introducing the acidizing fluid into a subterranean formation; and monitoring a characteristic of the acidizing fluid using an opticoanalytical device. In some embodiments, the opticoanalytical device can be in optical communication with a flow pathway for transporting the acidizing fluid.

In some embodiments, the methods can further comprise performing an acidizing operation in the subterranean formation, and monitoring a characteristic of the acidizing fluid or a formation fluid after the acidizing fluid is introduced into the subterranean formation using another opticoanalytical device. In such embodiments, the opticoanalytical device can be located in the subterranean formation or in optical communication with a flow pathway for transporting a flow back fluid produced from the subterranean formation. In some embodiments, the characteristic of the acidizing fluid being introduced into the subterranean formation can be adjusted in response to the characteristic of the acidizing fluid or formation fluid being monitored using the opticoanalytical device in the subterranean formation or monitoring the flow back fluid.

In some embodiments, methods described herein can comprise: forming an acidizing fluid on-the-fly by adding at least one acid to a base fluid stream; introducing the acidizing fluid into a subterranean formation; and monitoring a characteristic of the acidizing fluid using an opticoanalytical device while the acidizing fluid is being introduced into the subterranean formation. In some embodiments, the methods can further comprise determining if the characteristic of the acidizing fluid being monitored using the opticoanalytical device makes the acidizing fluid suitable for being introduced into the subterranean formation, and, optionally, if the acidizing fluid is unsuitable, adjusting the characteristic of the acidizing fluid.

In some embodiments, methods for performing an acidizing operation can comprise: providing an acidizing fluid comprising a base fluid and at least one acid; introducing the acidizing fluid into a subterranean formation; allowing the acidizing fluid to perform an acidizing operation in the subterranean formation; and monitoring a characteristic of the acidizing fluid or a formation fluid using an opticoanalytical device. In some embodiments, the characteristic of the acidizing fluid or the formation fluid can be monitored in-process within the subterranean formation, in a flow back fluid produced from the subterranean formation, or both.

In some embodiments, monitoring a characteristic of the acidizing fluid can comprise monitoring at least the identity and concentration of the at least one acid in the acidizing fluid, the flow back fluid, or both. In some embodiments, the methods can further comprise determining if the characteristic of the acidizing fluid being introduced into the subterranean formation needs to be adjusted in response to the concentration of the at least one acid being monitored using the opticoanalytical device in the subterranean formation or in optical communication with a flow pathway for transporting a flow back fluid produced therefrom. In some embodiments, the methods can further comprise adjusting the characteristic of the acidizing fluid being introduced into the subterranean formation. In some embodiments, determining if the characteristic of the acidizing fluid needs to be adjusted and adjusting the characteristic of the acidizing fluid can take place automatically under computer control.

In some embodiments, the methods can further comprise monitoring a characteristic of the acidizing fluid using an opticoanalytical device before the acidizing fluid is introduced into the subterranean formation. In some embodiments, the opticoanalytical device can be in optical communication with a flow pathway for transporting the acidizing fluid. In some embodiments, a change in concentration of at least one acid or other component in the acidizing fluid can be determined by monitoring the acidizing fluid before and after it is introduced into the subterranean formation. In some embodiments, the change in concentration of the at least one acid or other component in the acidizing fluid can be correlated to an effectiveness of an acidizing operation being conducted in the subterranean formation.

In some embodiments, a tracer or probe in the acidizing fluid or the flow back fluid can be monitored using an opticoanalytical device according to the present methods.

In some embodiments, methods described herein can comprise: providing an acidizing fluid comprising a base fluid and at least one acid; introducing the acidizing fluid into a subterranean formation; and monitoring a characteristic of the acidizing fluid using an opticoanalytical device before the acidizing fluid is introduced into the subterranean formation. In some embodiments, the opticoanalytical device can be in optical communication with a flow pathway for transporting the acidizing fluid.

In some embodiments, the methods can further comprise determining if the characteristic of the acidizing fluid being introduced into the subterranean formation needs to be adjusted in response to the characteristic of the acidizing fluid being monitored using the opticoanalytical device. In some embodiments, the methods can further comprise adjusting the characteristic of the acidizing fluid. In some embodiments, determining if the characteristic of the acidizing fluid needs to be adjusted and adjusting the characteristic of the acidizing fluid can take place automatically under computer control.

In some embodiments, the methods can further comprise monitoring a characteristic of the acidizing fluid or a formation fluid in-process using an opticoanalytical device, where the characteristic is measured in the subterranean formation, in a flow back fluid produced from the subterranean formation, or both.

Monitoring of Bacteria

In some embodiments, the methods described hereinabove can be extended to the monitoring of bacteria in a fluid, particularly a treatment fluid in a subterranean formation or being introduced into a subterranean formation. The monitoring of bacteria in or near real-time is presently believed to be unfeasible using current spectroscopic techniques, particularly at low bacterial levels. The present methods can overcome this limitation in the art.

In particular regard to subterranean operations, water used in various subterranean operations can be obtained from a number of "dirty" water sources, having varying levels of bacterial contamination therein. Although bacterial contamination may not be particularly problematic in treatment fluid when it is on the surface, once the treatment fluid is introduced into a warm subterranean environment, even low levels of bacteria can multiply quickly, potentially leading to damage of the subterranean formation. In some cases, biofouling of the surface of the subterranean formation can occur. Specifically, anaerobic $H_2S$-producing bacteria, can be particularly detrimental to subterranean operations. Rapidly multiplying bacteria, and their metabolic byproducts can quickly clog and corrode production tubulars, plug formation fractures and produce $H_2S$ which presents a health hazard and can lead to completion failure and loss of production. Accordingly, it is highly desirable to reduce bacteria levels in a treatment fluid before it is introduced into a subterranean formation.

A number of techniques are known for killing bacteria to reduce bacterial loads in a sample (e.g., exposure to ultraviolet light, ozonolysis, electrocoagulation, biocidal treatments and the like). However, it is believed that no current techniques are available for real-time or near real-time monitoring of bacterial load and for monitoring the effectiveness of a bactericidal treatment process to determine if bacterial load in a sample has been reduced to a sufficient degree. Without being bound by theory or mechanism, it is believed that bactericidal treatments such as, for example, ultraviolet light exposure, rapidly alter the deoxyribonucleic acid (DNA) and/or ribonucleic acid (RNA) of the bacteria, sometimes in conjunction with rupturing of their cell walls, to result in their eventual death.

In some embodiments, opticoanalytical devices described herein can be used to monitor bacteria according to the present embodiments by monitoring the DNA or RNA of the bacteria, and the changes thereto, as a result of a bactericidal treatment. The opticoanalytical devices, in some embodiments, can be configured for detecting the DNA or RNA of live bacteria, and the increase or decrease in the amount of DNA or RNA can be used to effectively monitor the amount of live bacteria in the sample. In some embodiments, the opticoanalytical devices can be configured to detect the DNA or RNA of specific types of bacteria. In some embodiments, fluorescent emission from the DNA or RNA can be used as an extremely sensitive detection technique for the DNA or RNA. Thus, the present methods can be suitable for fluids having low bacterial loads (e.g., as low as about 1000 bacteria/mL). As increasing numbers of bacteria have their DNA or RNA changed by the bactericidal treatment, the amount detected by the opticoanalytical devices will correspondingly decrease. The decrease in the amount of DNA or RNA can be directly correlated to the number of viable bacteria in the sample. Correspondingly, if it observed that the amount of DNA or RNA in a sample is increasing, the increase can be indicative of bacterial growth, which can suggest the necessity for performing a bactericidal treatment. In alternative embodiments, dead or dying bacteria that have altered DNA or RNA can also be monitored by the present methods, provided that the opticoanalytical device is configured for the altered DNA or RNA of these species.

In some embodiments, methods described herein can comprise: monitoring bacteria in water using an opticoanalytic device that is in optical communication with the water. In some embodiments, the water can be flowing through a flow pathway while monitoring the bacteria takes place. In some embodiments, the bacteria can be live bacteria. In other embodiments, the bacteria can be dead or dying bacteria. In some embodiments, monitoring can take place on a static water sample. In other embodiments, monitoring can take place while the water is flowing through a flow pathway.

In some embodiments, methods for monitoring bacteria can comprise: exposing water to a bactericidal treatment; and after exposing the water to the bactericidal treatment, monitoring live bacteria in the water using an opticoanalytical device that is in optical communication with the water.

In some embodiments, the monitoring live bacteria in the water can comprise monitoring DNA or RNA from the live bacteria. As noted previously, the DNA or RNA of the live bacteria can be distinguished from the DNA or RNA of dead, dying or non-viable bacteria due to a structural change affected by a bactericidal treatment in some embodiments, the present methods can comprise detecting and analyzing an emission of fluorescent radiation from the live bacteria (e.g., from the DNA or RNA of the live bacteria). In some or other embodiments, non-viable bacteria (i.e., dead or dying bacteria) can be monitored according to the present methods by utilizing the fingerprint of their altered DNA or RNA.

In some embodiments, monitoring the live bacteria in the water can comprise monitoring the types of bacteria, the quantity of bacteria, or both in the water. In some embodiments, it may be of interest to determine if specific types of bacteria are in the water, and the opticoanalytical devices can be specifically configured to detect different types of bacteria. based upon differences in their DNA or RNA "fingerprint." In other embodiments, it may be more of interest to simply determine the number of bacteria in the water i.e., the bacterial toad), and the present methods can be used in this regard as well by configuring the opticoanalytical devices for less specific DNA or RNA detection.

Illustrative bactericidal treatments can include, for example, exposure of the bacteria to ultraviolet light, electrocoagulation, ozonolysis, or introduction of a chemical biocide to the water. In particular, exposure to ultraviolet light can be an especially facile mechanism for killing bacteria, since a very rapid alteration of their DNA or RNA can occur upon exposure to ultraviolet light. Various illustrative bactericidal treatments are described in more detail in commonly owned U.S. Pat. No. 7,332,094, which is incorporated herein by reference in its entirety, and in commonly owned U.S. patent applications Ser. No. 12/683,337 (U.S. Patent Application Publication 2011/0163046) and 12/683, 343 (U.S. Patent Application Publication 2011/0166046), each of which is incorporated herein by reference in its entirety, In some embodiments, the methods can further comprise determining a kill ratio for the bacteria that has been affected by the bactericidal treatment. The kill ratio can be determined, in some embodiments, by measuring the live bacterial load before and after a bactericidal treatment is performed. In some embodiments, the kill ratio can be at least about 75%. In other embodiments, the kill ratio can be at least about 80%, or at least about 85%, or at least about 90%, or at least about 95%, or at least about 96%, or at least about 97%, or at least about 98%, or at least about 99%, in some embodiments, if a desired kill ratio is not attained, the methods can further comprise repeating the bactericidal treatment or performing a different bactericidal treatment.

In other embodiments, methods for monitoring bacteria can comprise: monitoring live bacteria in a water source using an opticoanalytical device that is in optical communication with the water source; and after monitoring the live bacteria in the water source, exposing the water to a bactericidal treatment. In some embodiments, the methods can further comprise monitoring the live bacteria in the water using an opticoanalytical device that is in optical communication with the water after the bactericidal treatment takes place.

In some embodiments, the present methods can further comprise determining if the water is suitable for being introduced into a subterranean formation. In some embodiments, determining if the water is suitable can be based upon the total number of live bacteria in the water. For example, if an excessive number of live bacteria are detected, the water can be unsuitable. In some embodiments, determining if the water is suitable can be based upon the presence of certain types of bacteria in the water, particularly above a given bacterial load. For example, the presence of $H_2S$-producing bacteria in the water can make the water unsuitable for being introduced into a subterranean formation. In addition, the mere presence of certain types of bacteria, in the water can make the water unsuitable for being introduced into a subterranean formation.

In some embodiments, the present methods can further comprise forming a treatment fluid comprising the water and at least one additional component; and introducing the treatment fluid into a subterranean formation. In alternative embodiments, a water that is suitable for being introduced into subterranean formation can be directly introduced into a subterranean formation without forming a treatment fluid (e.g., for a water flooding operation). In some embodiments, the present methods can further comprise monitoring the treatment fluid in the subterranean formation using another opticoanalytical device located in the subterranean formation. In some embodiments, the opticoanalytical device can be used to monitor live bacteria in the treatment fluid and determine if a bactericidal treatment needs to be applied to the treatment fluid in the subterranean formation. In other embodiments, the opticoanalytical device in the subterranean formation can be used to monitor another characteristic of the treatment fluid according to the embodiments previously described herein.

In some embodiments, methods for monitoring bacteria can comprise: providing a treatment fluid comprising a base fluid and at least one additional component; monitoring live bacteria in the treatment fluid using an opticoanalytical device that is in optical communication with a flow pathway for transporting the treatment fluid; and after monitoring the live bacteria in the treatment fluid, introducing the treatment fluid into a subterranean formation after monitoring the live bacteria therein. In some embodiments, the treatment fluid can be flowing in the flow pathway while monitoring the bacteria takes place. In other embodiments, the treatment fluid can be static while monitoring the bacteria.

In some embodiments, the present methods can further comprise determining a bactericidal treatment for the treatment fluid based upon the types of bacteria and the quantity of bacteria therein, as monitored using the opticoanalytical device, and performing the bactericidal treatment on the treatment fluid. In some embodiments, determining a bactericidal treatment for the treatment fluid can take place automatically under computer control. For example, based upon the types and number of bacteria in the treatment fluid, an artificial neural network can determine appropriate bactericidal treatment times, concentrations, and the like to predict how bacterial loads can be reduced in a treatment fluid. In some embodiments, the methods can further comprise monitoring live bacteria in the treatment fluid using an opticoanalytical device after performing the bactericidal treatment on the treatment fluid. Monitoring the bacteria in the treatment fluid after performing the bactericidal treatment can be used to assess the effectiveness of the bactericidal treatment prior to introducing the treatment fluid into the subterranean formation.

In some embodiments, the methods can further comprise monitoring live bacteria in the treatment fluid while the treatment fluid is located in a subterranean formation by using another opticoanalytical device located in the subterranean formation. In some embodiments, the opticoanalytical device in the subterranean formation can be used to determine if bacterial loads in the subterranean formation have exceeded desired levels. In some embodiments, based upon the bacteria monitored in the subterranean formation, the present methods can further comprise adding a bactericidal agent to the treatment fluid in the subterranean formation.

In some embodiments, methods for monitoring bacteria can comprise: providing a treatment fluid comprising a base fluid and at least one additional component; introducing the treatment fluid into a subterranean formation; and monitoring live bacteria in the treatment fluid within the subterranean formation using an opticoanalytical device located therein. In some embodiments, the methods can further comprise adding a bactericidal agent to the treatment fluid within the subterranean formation. In some embodiments, the methods can further comprise monitoring live bacteria in the treatment fluid within the subterranean formation using the opticoanalytical device therein after adding the bactericidal agent.

Monitoring of Fluid Streams

More generally, methods described hereinabove using opticoanalytical devices for monitoring treatment fluids and various components therein can be extended to monitoring the characteristics of fluid streams, particularly fluid streams that are being modified by an operator or under computer control, particularly remote monitoring by an operator or artificial neural network, in order to produce a desired effect in the fluid stream. As previously noted, fluid streams can be operatively linked to a great number of industrial processes, and the ability to monitor such fluids can be a significant process advantage, particularly when the monitoring can be conducted in-process. For example, fluids can change over time as a result of their use in an industrial process (or simply degrade), and the ability to rapidly monitor and respond to these changes can greatly improve process efficiency. Specifically, in some embodiments, opticoanalytical devices can be used to determine when a fluid needs to be replaced by monitoring its characteristics. In other embodiments, opticoanalytical devices can be used to determine when a fluid needs to be treated in order to adjust its characteristics, and in further embodiments, the opticoanalytical devices can be used to monitor an action taken to adjust the characteristics of the fluid.

In some embodiments, methods for monitoring a fluid can comprise: providing a fluid in a fluid stream; and monitoring a characteristic of the fluid using an opticoanalytical device that is in optical communication with the fluid in the fluid stream. In some embodiments, the methods can further comprise determining if the characteristic of the fluid needs to be adjusted based upon an output of the opticoanalytical device, and, optionally, if the characteristic of the fluid needs to be adjusted, performing an action on the fluid in the fluid stream to adjust the characteristic of the fluid.

In general, an action that can be taken on a fluid in order to adjust its characteristics can include any chemical, physical, or biological process that is undertaken in order to adjust its properties. Any combination or chemical, physical and/or biological processes can be used to adjust the characteristics of the fluid. In some embodiments, an action that can be performed on a fluid can comprise adding at least one component to the fluid or increasing the concentration of the component in the fluid. For example, in non-limiting embodiments, an acid can be added or increased in concentration to lower the pH of a fluid, or a viscosifying agent can be added or increased in concentration to modify the rheological properties of a fluid. In some embodiments, an action that can be performed on a fluid can comprise removing at least one component from the fluid or reducing the concentration of the component in the fluid. For example, in non-limiting embodiments, a fluid can be subjected to ion exchange to remove ionic species therefrom, or a filtration step can be conducted to remove particulate matter from the fluid. In still other embodiments, an action that can be performed on a fluid can comprise exposing the fluid to a bactericidal treatment or another type of purification treatment known in the art. As described above, bacterial growth in fluids can present significant issues. Bactericidal treatments can include any of those set forth previously hereinabove. It is to be recognized that the foregoing examples of actions that can be performed on a fluid in order to adjust its characteristics should be considered illustrative in nature only, and one having ordinary skill in the art will be able to select an appropriate action to perform on a fluid in order to affect its properties in a desired way.

In some embodiments, after an action has been performed on the fluid in order to modify its characteristics, the fluid can again be monitored with an opticoanalytical device to determine if the action taken has had the desired effect. In some embodiments, the present methods can comprise monitoring a characteristic of the fluid using an opticoanalytical device that is in optical communication with the fluid in the fluid stream, after an action has been taken on the fluid to modify its characteristics. Accordingly, if the characteristic of the fluid has been modified in a desired way and returned to an in-range value, use of the fluid can continue. Likewise, if the characteristic of the fluid has not been returned to an in-range value, the action can again be performed on the fluid or a different action can be selected to be performed on the fluid.

In some embodiments, various operations in the monitoring of the characteristics of a fluid can take place automatically under computer control. In some embodiments, computer control can be used to determine if the characteristic of the fluid needs to be adjusted. In some embodiments, an action can be performed on the fluid to adjust the characteristic. In some embodiments, the action performed on the fluid can take place under computer control. For example, computer control can be used to assess an out of range characteristic in a fluid and determine an appropriate corrective course of action. Thereafter, computer control can be used to automatically carry out the action used for adjusting the characteristic of the fluid.

In general, any type of fluid in a fluid stream can be monitored according to the present embodiments. Fluids suitable fir use in the present embodiments can include, for example, flowable solids, liquids and/or gases. In some embodiments, the fluid can be water or an aqueous fluid containing water. In other embodiments, the fluid can comprise an organic compound, specifically a hydrocarbon, an oil, a refined component of oil, or a petrochemical. Furthermore, the fluids streams can be operatively coupled to any type of process or used in any type of industrial setting. For example, in some embodiments, the fluid stream can comprise a water stream that is operatively coupled to a cooling tower or like heat transfer mechanism. In other embodiments, the fluid stream can be located in a refinery or chemical plant. When used in such locations, the fluid stream can comprise a coolant stream in some embodiments, a reactant feed stream in some embodiments, or a product feed stream in other embodiments. Thus, the present methods can be used to confirm that the correct materials are being supplied to and produced from an industrial process, as well as monitor background fluid use that is used in carrying out the process.

In some embodiments, methods for monitoring a fluid can comprise: providing a fluid in a fluid stream; monitoring a characteristic of the fluid using an opticoanalytical device that is in optical communication with the fluid in the fluid stream; determining if the characteristic of the fluid needs to be adjusted based upon an output from the opticoanalytical device; performing an action on the fluid in the fluid stream so as to adjust the characteristic; and after performing the action on the fluid in the fluid stream, monitoring the characteristic of the fluid using another opticoanalytical device that is in optical communication with the fluid in the fluid stream.

In some embodiments, methods for monitoring water can comprise: providing water in a fluid stream; performing an action on the water in the fluid stream so as to adjust a characteristic of the water; after performing the action on the water in the fluid stream, monitoring the characteristic of the water using an opticoanalytical device that is in optical communication with the water in the fluid stream; and determining if the characteristic of the water lies within a desired range. In some embodiments, performing an action on the water can comprise at least one action such as, for example, adding at least one component to the water or increasing the concentration of the component, removing at least one component from the water or reducing the concentration of the component, exposing the water to a bactericidal treatment or another purification treatment, and any combination thereof. In some embodiments, the methods can further comprise repeating the action on the water or performing another action on the water, if the characteristic of the water does not lie in a desired range. In some embodiments, determining if the characteristic of the water lies within a desired range and repeating the action on the water and/or performing another action on the water can take place automatically under computer control.

Although a number of industrial processes use and produce fluids, it is believed that the present methods can be particularly beneficial in cooling tower and refinery applications. In both of these applications, it can be important to maintain fluid integrity during fluid input and output. In regard to refinery applications, the present methods can be applied to monitoring the fluid input and output of the material being refined being refined. For example, in some embodiments, opticoanalytical devices can be used to monitor very viscous fluids such as 30 gravity oil in order to monitor process integrity.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed, in particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
   providing at least one source material;
   combining the at least one source material with a base fluid to form a treatment fluid; and
   monitoring a characteristic of the treatment fluid using a first integrated computational element in a first optical computing device that is in optical communication with a flow pathway for transporting the treatment fluid, the first integrated computational element being located on a rotating disc;
   wherein the first integrated computational element is configured to optically interact with the fluid and thereby generate optically interacted light so that a portion of the optically interacted light is transmitted through the first integrated computational element;
   wherein the first integrated computational element comprises two or more materials deposited in layers such that the first integrated computational element has transmissive, reflective, or absorptive properties that are configured for specifically detecting and analyzing the characteristic of the treatment fluid; and
   wherein the first integrated computational element separates electromagnetic radiation related to the characteristic of the treatment fluid from electromagnetic radiation that is not, the electromagnetic radiation that is related to the characteristic of the treatment fluid being received by a detector after separation.

2. The method of claim 1, further comprising:
   before combining, monitoring a characteristic of the at least one source material using a second integrated computational element in a second optical computing device that is in optical communication with a flow pathway for transporting the at least one source material;
   wherein the second integrated computational element comprises two or more materials deposited in layers such that the second integrated computational element has transmissive, reflective, or absorptive properties that are configured for specifically detecting and analyzing the characteristic of the at least one source material; and
   wherein the second integrated computational element separates electromagnetic radiation related to the characteristic of the at least one source material from electromagnetic radiation that is not, the electromagnetic radiation that is related to the at least one source material being received by a detector after separation.

3. The method of claim 1, wherein the treatment fluid comprises an aqueous treatment fluid.

4. The method of claim 1, further comprising:
transporting the treatment fluid to a pump; and
introducing the treatment fluid into a subterranean formation.

5. The method of claim 4, further comprising:
monitoring a characteristic of the treatment fluid using a second integrated computational element in a second optical computing device that is in optical communication with the flow pathway for transporting the treatment fluid;
wherein the second integrated computational element in the second optical computing device is located at the pump; and
wherein the second integrated computational element comprises two or more materials deposited in layers such that the second integrated computational element has transmissive, reflective, or absorptive properties that are configured for specifically detecting and analyzing the characteristic of the treatment fluid; and
wherein the second integrated computational element separates electromagnetic radiation related to the characteristic of the treatment fluid from electromagnetic radiation that is not, the electromagnetic radiation that is related to the characteristic of the treatment fluid being received by a detector after separation.

6. The method of claim 5, further comprising:
determining if the characteristic of the treatment fluid being monitored using either the first integrated computational element in the first optical computing device or the second integrated computational element in the second optical computing device makes the treatment fluid suitable for being introduced into the subterranean formation; and
adjusting the characteristic of the treatment fluid if needed.

7. The method of claim 6, wherein determining if the characteristic of the treatment fluid makes the treatment fluid suitable and adjusting the characteristic of the treatment fluid both occur automatically under computer control.

8. The method of claim 5, wherein transporting the treatment fluid takes place by boat or barge to an offshore job site.

9. The method of claim 1, further comprising:
introducing the treatment fluid into a subterranean formation.

10. The method of claim 9, further comprising:
while the treatment fluid is in the subterranean formation, monitoring a characteristic of the treatment fluid or a formation fluid using a second integrated computational element in a second optical computing device that is located in the subterranean formation;
wherein the second integrated computational element comprises two or more materials deposited in layers such that the second integrated computational element has transmissive, reflective, or absorptive properties that are configured for specifically detecting and analyzing the characteristic of the treatment fluid or the formation fluid; and
wherein the second integrated computational element separates electromagnetic radiation related to the characteristic of the treatment fluid or the formation fluid from electromagnetic radiation that is not, the electromagnetic radiation that is related to the characteristic of the treatment fluid or the formation fluid being received by a detector after separation.

11. The method of claim 9, further comprising:
producing a flow back fluid from the subterranean formation; and
monitoring a characteristic of the flow back fluid or a produced formation fluid using a second integrated computational element in a second optical computing device that is in optical communication with a flow pathway for transporting the flow back fluid;
wherein the second integrated computational element comprises two or more materials deposited in layers such that the second integrated computational element has transmissive, reflective, or absorptive properties that are configured for specifically detecting and analyzing the characteristic of the flow back fluid or the produced formation fluid; and
wherein the second integrated computational element separates electromagnetic radiation related to the characteristic of the flow back fluid or the produced formation fluid from electromagnetic radiation that is not, the electromagnetic radiation that is related to the characteristic of the flow back fluid or the produced formation fluid being received by a detector after separation.

12. The method of claim 9, further comprising:
adjusting the characteristic of the treatment fluid being introduced into the subterranean formation in response to a characteristic of the treatment fluid being monitored using a second integrated computational element in a second optical computing device that is in optical communication with a flow pathway for transporting the treatment fluid;
wherein the second integrated computational element in the second optical computing device is located at a pump used for introducing the treatment fluid into the subterranean formation; and
wherein the second integrated computational element comprises two or more materials deposited in layers such that the second integrated computational element has transmissive, reflective, or absorptive properties that are configured for specifically detecting and analyzing the characteristic of the treatment fluid; and
wherein the second integrated computational element separates electromagnetic radiation related to the characteristic of the treatment fluid from electromagnetic radiation that is not, the electromagnetic radiation that is related to the characteristic of the treatment fluid being received by a detector after separation.

13. The method of claim 12, wherein adjusting the characteristic of the treatment fluid being introduced into the subterranean formation occurs automatically under computer control.

14. A method comprising:
preparing a treatment fluid;
transporting the treatment fluid to a job site;
introducing the treatment fluid into a subterranean formation at the job site;
monitoring a characteristic of the treatment fluid at the job site using a first integrated computational element in a first optical computing device that is in optical communication with a flow pathway for transporting the treatment fluid, the first integrated computational element being located on a rotating disc;

wherein the first integrated computational element is configured to optically interact with the fluid and thereby generate optically interacted light so that a portion of the optically interacted light is transmitted through the first integrated computational element;

wherein the first integrated computational element comprises two or more materials deposited in layers such that the first integrated computational element has transmissive, reflective, or absorptive properties that are configured for specifically detecting and analyzing the characteristic of the treatment fluid; and wherein the first integrated computational element separates electromagnetic radiation related to the characteristic of the treatment fluid from electromagnetic radiation that is not, the electromagnetic radiation that is related to the characteristic of the treatment fluid being received by a detector after separation;

determining if the characteristic of the treatment fluid being monitored using the first integrated computational element in the first optical computing device makes the treatment fluid suitable for being introduced into the subterranean formation; and adjusting the characteristic of the treatment fluid if needed.

15. The method of claim 14, wherein the treatment fluid comprises an aqueous treatment fluid.

16. The method of claim 14, wherein determining if the characteristic of the treatment fluid makes the treatment fluid suitable and adjusting the characteristic of the treatment fluid both occur automatically under computer control.

17. The method of claim 14, further comprising:

performing a treatment operation in the subterranean formation; and monitoring a characteristic of the treatment fluid or a formation fluid after the treatment fluid is introduced into the subterranean formation using a second integrated computational element in a second optical computing device that is located in the subterranean formation or is in optical communication with a flow pathway for transporting a flow back fluid produced therefrom;

wherein the second integrated computational element comprises two or more materials deposited in layers such that the second integrated computational element has transmissive, reflective, or absorptive properties that are configured for specifically detecting and analyzing the characteristic of the treatment fluid or the formation fluid; and wherein the second integrated computational element separates electromagnetic radiation related to the characteristic of the treatment fluid or the formation fluid from electromagnetic radiation that is not, the electromagnetic radiation that is related to the characteristic of the treatment fluid or the formation fluid being received by a detector after separation.

18. The method of claim 17, further comprising:

adjusting the characteristic of the treatment fluid being introduced into the subterranean formation in response to the characteristic of the treatment fluid or the formation fluid being monitored using the second integrated computational element in the second optical computing device.

19. The method of claim 17, wherein the treatment fluid being monitored with the second integrated computational element in the second optical computing device is at least partially spent.

20. The method of claim 14, wherein transporting the treatment fluid takes place by boat or barge to an offshore job site.

21. A method comprising:

forming a treatment fluid on-the-fly by adding at least one component to a base fluid stream;

introducing the treatment fluid into a subterranean formation; and monitoring a characteristic of the treatment fluid using an integrated computational element in an optical computing device while the treatment fluid is being introduced into the subterranean formation, the integrated computational element being located on a rotating disc;

wherein the integrated computational element is configured to optically interact with the fluid and thereby generate optically interacted light so that a portion of the optically interacted light is transmitted through the integrated computational element;

wherein the integrated computational element comprises two or more materials deposited in layers such that the integrated computational element has transmissive, reflective, or absorptive properties that are configured for specifically detecting and analyzing the characteristic of the treatment fluid; and wherein the integrated computational element separates electromagnetic radiation related to the characteristic of the treatment fluid from electromagnetic radiation that is not, the electromagnetic radiation that is related to the characteristic of the treatment fluid being received by a detector after separation.

22. The method of claim 21, further comprising:

determining if the characteristic of the treatment fluid being monitored using the integrated computational element in the optical computing device makes the treatment fluid suitable for being introduced into the subterranean formation; and adjusting the characteristic of the treatment fluid if needed.

* * * * *